United States Patent [19]

Dörreich et al.

[11] Patent Number: 5,585,256
[45] Date of Patent: Dec. 17, 1996

[54] ASPERGILLUS ACULEATUS RHAMNOGALACTURON ACETYL ESTERASES, DNA SEQUENCES ENCODING THE ENZYMES AND METHODS OF USE THEREOF

[75] Inventors: Kurt Dörreich, Grenzach-Wyhelen, Germany; Flemming M. Christensen, Rungsted Kyst, Denmark; Yvette Schnell, Roschenz; Marcel Mischler, Himmelried, both of Switzerland; Henrik Dalbøge; Hans P. Heldt-Hansen, both of Virum, Denmark

[73] Assignee: Novo Nordisk A/S, Bagsvaerd, Denmark

[21] Appl. No.: 313,050

[22] PCT Filed: Mar. 29, 1993

[86] PCT No.: PCT/DK93/00109

§ 371 Date: Oct. 5, 1994

§ 102(e) Date: Oct. 5, 1994

[87] PCT Pub. No.: WO93/20190

PCT Pub. Date: Oct. 14, 1993

[30] Foreign Application Priority Data

Mar. 27, 1992 [DK] Denmark .................................. 0420/92

[51] Int. Cl.$^6$ .............................. C12N 9/18; C12N 15/55; C12N 15/80; C12P 7/40
[52] U.S. Cl. ........................ 435/197; 435/196; 435/69.1; 435/252.3; 435/252.33; 435/254.3; 435/137; 536/23.2; 935/14; 935/28; 935/68; 935/72
[58] Field of Search ..................... 435/195, 196, 435/197, 69.1, 252.3, 320.1, 254.3, 137; 536/23.2

[56] References Cited

U.S. PATENT DOCUMENTS 4,200,694   4/1980   Ishii et al. .............................. 435/101
4,652,639   3/1987   Stabinsky ............................ 435/91.52

FOREIGN PATENT DOCUMENTS 0075444   3/1983   European Pat. Off. .
0080827   11/1982  WIPO .
0339011   4/1989   WIPO .

OTHER PUBLICATIONS

Henk A. Schols et al., Carbohydrate Research, vol. 206, pp. 105–115, 1990.
Williamson et al., Dialog Information Services, Carbohydr Polym 13 (4), 387–398, 1990 (Abstract Only).
Williamson, G., et al., 1990, Carbohydrate Polymers, 13: 387–397.
Fort Kamp, E., et al., 1986 DNA, 5(6):511–517.
Massiot, P., et al., 1990, Food Biotechnology, 4(1):364 (Abstract).
Khanh, N. Q., et al., 1990, Nucleic Acids Research, 18(14): 4262.
Mutter, M. et al., 1994, Plant Physiology, 106:347–349.
Searle–van Leeuwen, M. J. F., 1992, Applied Microbiology and Biotechnology, 38:347–349.

Primary Examiner—Robert A. Wax
Assistant Examiner—William W. Moore
Attorney, Agent, or Firm—Steve T. Zelson, Esq.; Elias J. Lambiris, Esq.

[57] ABSTRACT

The present invention relates to rhamnogalacturon acetyl esterases derived from *Aspergillus aculeatus* and DNA Sequences encoding the enzymes. The present invention also relates to the use of rhamnogalacturon acetyl esterases for degrading modified hairy region.

28 Claims, 11 Drawing Sheets

RGA1/5'-END

```
                                                                          48
AGT CTA TAA GAA GAT TGA CAG CCA AGA ACA CCA CCC ACA ATG AAG ACC
                                                  Met Lys Thr

96
GCC GCC TCT TGC ACC GCT CTT CTT CCT CCC CTC TGC CCT CGC CAC GAC
Ala Ala Ser Cys Thr Ala Leu Leu Pro Pro Leu Cys Pro Arg His Asp

144
NNG GTC TAT CTC GCG GGT GAC TCG ACC ATG GCC AAG AAT GGA GGC GGG
Xxx Val Tyr Leu Ala Gly Asp Ser Thr Met Ala Lys Asn Gly Gly Gly

192
TCG GGA ACT AAC GGC TGG GGC GAG TAC CTG CGA GTT ACC TCT CCG CGA
Ser Gly Thr Asn Gly Trp Gly Glu Tyr Leu Arg Val Thr Ser Pro Arg

215
CAG TGG TTA ACG ACG CGG TCG CG
Gln Trp Leu Thr Thr Arg Ser Arg
```

```
       Asp Ser Thr Met Ala Lys Asn Gly Gly
5' - GGAATTCC GAC AGI ACI ATG GCI AAA AAC GGI GG -
                    T TC        G   T
3'
```

FIG. 7

RGA1/5'-END

```
                                                                    48
AGT CTA TAA GAA GAT TGA CAG CCA AGA ACA CCA CCC ACA ATG AAG ACC
                                                    Met Lys Thr

96
GCC GCC TCT TGC ACC GCT CTT CTT CCT CTC TGC CCT CCC CAC GAC
Ala Ala Ser Cys Thr Ala Leu Leu Pro Leu Cys Pro Arg His Asp

144
NNG GTC TAT CTC CCG GGT GAC TCG ACC ATG GCC AAG AAT GGA GGC
Xxx Val Tyr Leu Ala Gly Asp Ser Thr Met Ala Lys Asn Gly Gly

192
TCG GGA ACT AAC GGC TGG GGC GAG TAC CTG CGA GTT ACC TCT CCG CGA
Ser Gly Thr Asn Gly Trp Gly Glu Tyr Leu Arg Val Thr Ser Pro Arg

215
CAG TGG TTA ACG CCG TCG CG
Gln Trp Leu Thr Thr Arg Ser Arg
```

FIG. 8

RGA1/3'-END

```
GAC GCA ACC TAT GAA GAC CTT GGA ATG CCA CCG TCA ACT CGT ATT CCC     48
Asp Ala Thr Tyr Glu Asp Leu Gly Met Pro Pro Ser Thr Arg Ile Pro

CAT CGA TCA CAC CCA CAC CAG TCC TGC CGC GGG AGG TGG TCG CTG AGC     96
His Arg Ser His Pro His Gln Ser Cys Gly Ala Arg Ser Trp Leu Ser

GTT CTT GAA GGC GGT ATG CAC CGG TAC GTC GTT GAA GAG TGT GTT        144
Val Leu Glu Gly Gly Met His Arg Tyr Val Val Glu Glu Cys Val

GAC GAC GAC GAG CTT TGA CCG GAC ATG TCT GTG ATT GAG CAG ATG GAA    192
Asp Asp Asp Glu Leu ***

AGA CAA AGG AGT GGA CCG ATA AGG ACA GGA GTT GTC ATG TAT AGT GGT    240

ATC GAC AAA AAA AAA AAA AAA AAA AAA AAA AAA AAA AA                 275
```

FIG. 9

ASPERGILLUS ACULEATUS RHAMNOGALACTURON ACETYL ESTERASES, DNA SEQUENCES ENCODING THE ENZYMES AND METHODS OF USE THEREOF

CROSS-REFERENCE TO RELATED APPLICATIONS

This application is a continuation of PCT/DK/93/00109 filed Mar. 29, 1993, which is incorporated herein by reference.

The invention comprises a novel enzyme, which is a rhamnogalacturonan acetyl esterease (the abbreviation RGAE will usually be used in the following), a corresponding DNA sequence, a vector, a transformed host, a method for production of an RGAE, an enzyme preparation, and a use of the RGAE.

The invention provides the characterization, the detection and description of a novel RGAE, a partial amino acid sequence of this enzyme, partial DNA sequences, and a total amino acid sequence and a total DNA sequence.

RGAE is a hydrolase with the systematic enzyme name rhamnogalacturonan acetic-ester acetylhydrolase, which belongs to the group of acetyl esterases (EC no. 3.1.1.6), which catalyze the hydrolysis of acetic esters to the corresponding alcohols and acetate.

BACKGROUND OF THE INVENTION

Polysaccharides (e.g. pectins) from plants are frequently substituted with is acetyl groups (Rombouts, F. M., J. F. Thibault, C. Mercier, "Oxidative enzyme-catalyzed crosslinking of beet pectins", U.S. Pat. No. 4,672,034). In the applications of polysaccharides these substitutions influence the gelation properties (Williamson G., C. B. Faulds, J. A. Matthew, D. B. Archer, V. J. Morris, G. J. Brownsey, M. J. Ridout, "Gelation of sugarbeet and citrus pectins using enzymes extracted from orange peel", Carbohydrate Polymers 13, 387–397, 1990). In the processing of plant material, e.g. fruits and vegetables, endogenous enzymes are used as processing aids to improve yield and quality of the end product (Pilnik, W., A. G. J. Voragen., "Effect of enzyme treatment on the quality of processed fruits and vegetables", in: Jen J. J., "Quality factors of fruits and vegetables, chemistry and technology", ACS Symp. Ser. 405, American Chemical Society, Washington D.C., 250–269, 1989). Schols et al. isolated and characterized from apple cell walls an acidic polymeric pectin fragment by the use of a technical enzyme preparation containing pectolytic, hemicellulolytic and cellulolytic enzymes. This enzyme resistant polysaccharide, called "modified hairy region" (MHR) consists of a highly branched rhamnogalacturonan backbone, with acetyl groups on the galacturonic acid residues (Schols, H. A., M. A. Posthumus, A. G. J. Voragen, "Structural features of hairy regions of pectins isolated from apple juice produced by the liquefaction process", Carbohydrate Research, 206, 117–129, 1990). Extensive screening of commercial enzyme preparations have led to an *Aspergillus aculeatus* preparation, which was able to degrade MHR. A novel enzyme called rhamnogalacturonase (RG) was identified and purified from this preparation. During the purification of RG it became obvious that the enzyme works only on saponified MHR and that therefore esterases, particularly acetyl esterases, must play an important role for the degradation of MHR (Schols, H. A., C. C. J. M. Geraeds, M. J. F. Searle-van Leuwen, F. J. M. Kormelink, A. G. J. Voragen, "Rhamnogalacturonase: a novel enzyme that degrades the hairy regions of pectins", Carbohydrate research 206, 105–115, 1990). Enzymes which can deacetylate branched rhamnogalacturonans, like HMR, are therefore needed, as the high degree of acetylation on branched rhamnogalacturonans hinders the action of enzymes with higher activity on deacetylated rhamnogalacturonans.

Several polysaccharides (xylan, mannan and pectin) are known to be acetylated, and the acetyl esterases are known to be very specific against their specific polysaccharide substrate, but some of them exhibit activity on non-polysaccharide substrates, like triacetin and naphthol acetate. An *Aspergillus niger* acetylesterase, active towards triacetin and beet pectin, has been described by Mathew et al. (Mathew, J. A., S. J. Howson, M. H. J. Keenan, P. S. Belton, "Improvement of the gelation properties of sugarbeet pectin following treatment with an enzyme preparation derived from *Aspergillus niger*—Comparison with a chemical modification", Carbohydrate Polymers 12, 295–306, 1990). Pectin acetylesterase, highly active towards triacetin, has been purified from citrus peel (Wiliamson, G., "Purification and characterisation of pectin acetyl esterase from orange peel", Phytochemistry 30, 445–449, 1991 ). Activity on MHR has not been demonstrated for any of these prior art polysaccharide acetyl esterases.

Thus, the ability of acetyl esterases to hydrolyze the acetyl groups of HMR have not been demonstrated for any of the prior art acetyl esterases, and it is the purpose of the invention to provide an RGAE with high specificity towards HMR.

SUMMARY OF THE INVENTION

The RGAE according to the invention is characterized by the fact that it is immunologically reactive with an antibody raised against a purified RGAE derived from *Aspergillus aculeatus*, CBS 101.43.

In the present context, the term "derived from" is intended not only to indicate an RGAE produced by strain CBS 101.43, but also an RGAE encoded by a DNA sequence isolated from strain CBS 101.43 and produced in a host organism transformed with said DNA sequence.

A preferred embodiment of the RGAE according to the invention exhibits the following partial amino acid sequence

```
            1               5                    10                   15
         Asp—Arg—Val—Tyr—Leu—Ala—Gly—Asp—Ser—Thr—Met—Thr—Lys—Asn—Gly—
                        20                  25
         Gly—Xaa—Ser—Gly—Thr—Asn—Gly—Trp—Gly—Glu—Tyr—Leu—Ala—    (SEQ ID No. 1)
``` or a partial amino acid sequence homologous thereto, this partial amino acid sequence being part of a polypeptide with RGAE activity.

In the present context, the term "homologue" is intended to indicate a polypeptide encoded by DNA which hybridizes to the same probe as the DNA coding for the RGAE enzyme under certain specified conditions (such as presoaking in 5×SSC and prehybridizing for 1 hour at ~40° C. in a solution of 5×SSC, 5×Denhardt's solution, 50 mM sodium phosphate, pH 6.8, and 50 μg of denatured sonicated calf thymus DNA, followed by hybridization in the same solution supplemented with 50 μCi 32-P-dCTP labelled probe for 18 hours at ~40° C. followed by washing three times in 2×SSC, 0.2% SDS at 40° C. for 30 minutes). More specifically, the term is intended to refer to a DNA sequence which is at least 70% homologous to the sequence shown above encoding the RGAE of the invention. The term is intended to include modifications of the DNA sequence indicated above, such as nucleotide substitutions which do not give rise to another amino acid sequence of the RGAE but which correspond to the codon usage of the host organism into which the DNA construct is introduced or nucleotide substitutions which do give rise to a different amino acid sequence and therefore, possibly, a different protein structure which might give rise to an RGAE mutant with different properties than the native enzyme. Other examples of possible modifications are insertion of one or more nucleotides into the sequence, addition of one or more nucleotides at either end of the sequence, or deletion of one or more nucleotides at either end or within the sequence.

Thus, surprisingly it has been found that the RGAE according to the invention is highly specific for the deacetylation of MHR, but that it does not show any acitivity towards triacetin and beet pectin, and also it exhibits a higher specificity than the prior art acetyl esterases.

The above indicated partial amino acid sequence can be used for construction of DNA probes which can be used for screening a genomic library for organisms expressing such enzyme, or a cDNA library, thereby obtaining DNA sequences, which can be used either for an overproduction of RGAE, if inserted in the microorganism species, from which the parent DNA molecule originated, or for production of RGAE without accompanying closely related enzymes, if inserted in a host microorganism, which in its not-transformed condition does not produce any enzymes closely related to RGAE. The DNA sequences can be established otherwise, as will apppear from the following.

Thus, the purpose of the invention is the provision of a new RGAE and of means and methods for production of RGAE in better yield and higher purity than hitherto possible, and of a use of RGAE either alone or in combination with other significant amounts of enzymes for degradation of plant cell wall tissue, more efficient than hitherto possible. Also it is the purpose of the invention to provide novel products, wherein the proportion of the RGAE is either increased or decreased in relation to the proportion in the original product.

The recombinant DNA sequence obtainable according to the invention comprises a DNA sequence coding for a polypeptide having RGAE activity, or a DNA sequence having substantial sequence homology to such RGAE coding sequence.

BRIEF DESCRIPTION OF THE DRAWINGS

FIG. 7 compares the amino acid sequence of a rhamnogalacturonan acetylesterase from *Aspergillus aculeatus* with the nucleic acid sequence of a deoxyinosine-containing primer.

FIG. 8 shows a portion of the nucleotide sequence of the 5'-end of the rgal cDNA, and the deduced primary structure of RGAEase I from *A. aculeatus*.

FIG. 9 shows a portion of the nucleotide sequence of the 3'-end of the rgal cDNA and the deduced primary structure of RGAEase I from *A. aculeatus*.

Figure 1:
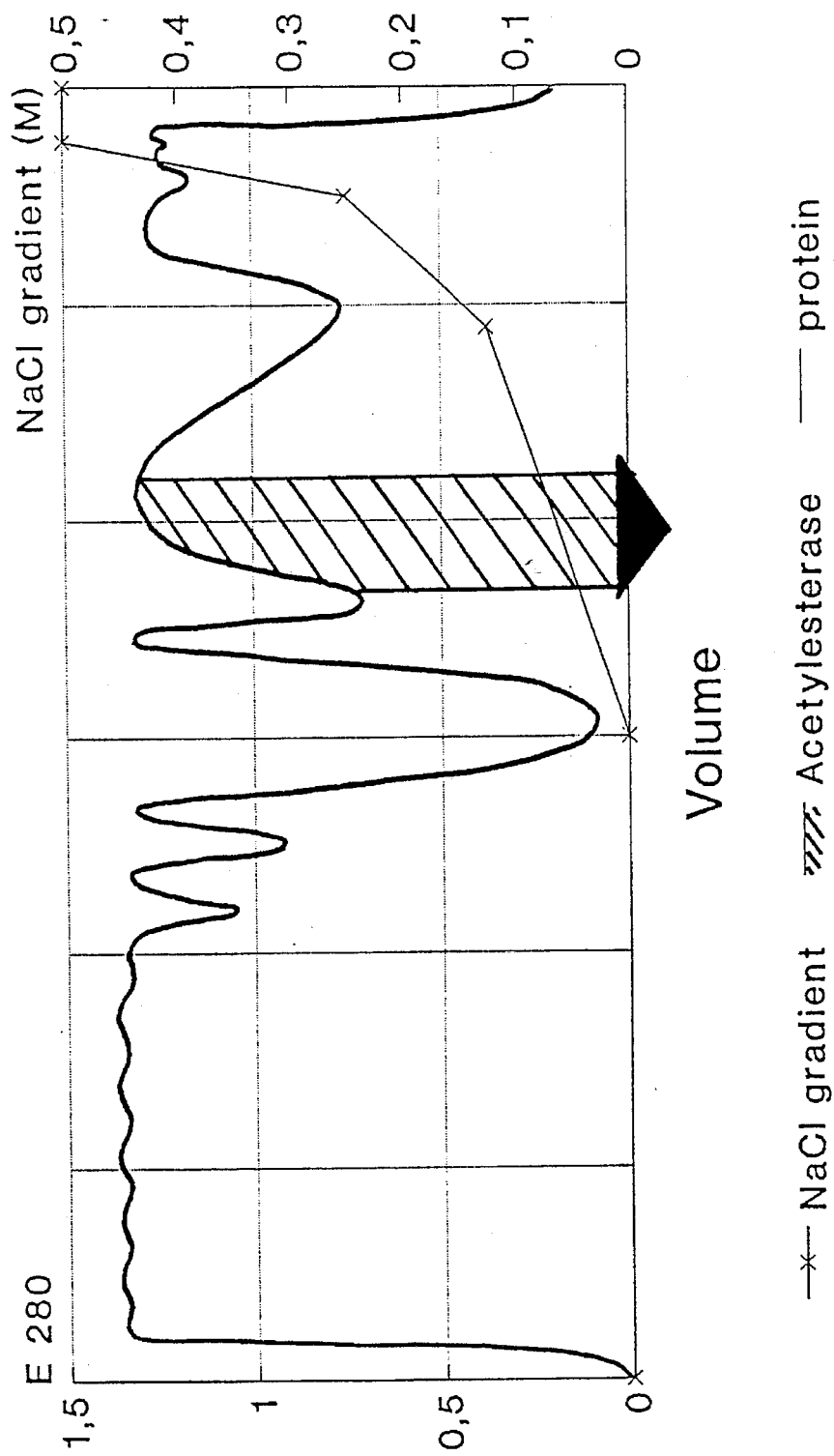
FIG. 1 shows an ion exchange chromatogram from which the rhamnogalacturonan acetyl esterase fraction is pooled from 0.04–0.08M NaCl (—x— NaCl gradient (M);///rhamnogalacturonan acetyl esterase;—protein).

In the following it will be explained in detail how the recombinant DNA sequence according to the invention can be produced.

Crude enzyme preparations produced from *Aspergillus aculeatus* for purification of the RGAE can be produced as follows. For the sake of brevity this crude *Aspergillus aculeatus* preparation will be referred to in the following as A.a.e.p.

The strain *Aspergillus aculeatus* CBS 101.43 as a gene donor was fermented in a pilot plant scale in the following way.

An agar substrate with the following composition was prepared in a Fernbach flask:

| | |
|---|---|
| Peptone Difco | 6 g |
| Aminolin Ortana | 4 g |
| Glucose | 1 g |
| Yeast extract Difco | 3 g |
| Meat extract Difco | 1.5 g |
| $KH_2PO_4$ Merck | 20 g |
| Malt extract Evers | 20 g |
| Ion exchanged $H_2O$ | ad 1000 ml | pH was adjusted to between 5.30 and 5.35. Then 40 g of Agar Difco was added, and the mixture was autoclaved for 20 minutes at 120° C. (the substrate is named E-agar).

The strain CBS 101.43 was cultivated on an E-agar slant (37° C.). The spores from the slant were suspended in sterilized skim-milk, and the suspension was lyophilized in vials. The contents of one lyophilized vial was transferred to the Fernbach flask. The flask was then incubated for 13 days at 30° C.

A substrate with the following composition was prepared in a 500 liter seed fermenter:

| | |
|---|---|
| $CaCO_3$ | 1.2 kg |
| Glucose | 7.2 kg |

-continued

| Rofec (corn steep liquor dry matter) | 3.6 kg |
|---|---|
| Soy bean oil | 1.2 kg |

Tap water was added to a total volume of around 240 liters. pH was adjusted to around 5.5 before addition of CaCO₃. The substrate was sterilized in the seed fermenter for 1 hour at 121° C. Final volume before inoculation was around 300 liters.

The Fernbach flask spore suspension was transferred to the seed fermenter. Seed fermentation conditions were:

Fermenter type: Conventional aerated and agitated fermenter with a height/diameter ratio of around 2.3.

| Agitation: | 300 rpm (two turbine impellers) |
|---|---|
| Aeration: | 300 normal liter air per minute |
| Temperature: | 30 to 31° C. |
| Time: | around 28 hours |

Around 28 hours after inoculation 150 liters was transferred from the seed fermenter to the main fermenter.

A substrate with the following composition was prepared in a 2500 liter main fermenter:

| Toasted soy meal | 90 kg |
|---|---|
| $KH_2PO_4$ | 20 kg |
| Pluronic ® antifoam agent | 150 ml |

Tap water was added to a total volume of around 900 liters. The toasted soy meal was suspended in water. pH was adjusted to 8.0 with NaOH, and the temperature was raised to 50° C. Thereafter around 925 Anson units of Alcalase® 0.6 L was added to the suspension. The mixture was held for 4 hours at 50° C. and pH=8.0 ($Na_2CO_3$ addition) with no aeration and 100 rpm agitation. Thereafter the remaining substrate components were added and pH was adjusted to around 6.0 with phosphoric acid. The substrate was sterilized in the main fermenter for 1½ hours at 123° C. Final volume before inoculation was around 1080 liters.

Then 150 liters of seed culture was added.

Fermentation conditions were:

Fermenter type: Conventional aerated and agitated fermenter with a height/diameter ratio of around 2.7.

| Agitation: | 250 rpm (two turbine impellers) |
|---|---|
| Aeration: | 1200 normal liter air per minute |
| Temperature: | 30° C. |
| Time: | around 151 hours |

From 24 fermentation hours to around 116 fermentation hours pectin solution was added aseptically to the main fermenter at a constant rate of around 8 liters per hour. The pectin solution with the following composition was prepared in a 500 liter dosing tank:

| Pectin genu*) | 22 kg |
|---|---|
| Phosphoric acid, conc. | 6 kg |
| Pluronic ® antifoam agent | 50 ml |

*)Genu pectin (citrus type NF from the Copenhagen pectin factory Ltd.)

Tap water was added to a total volume of around 325 liters. The substrate was sterilized in the dosing tank for 1 hour at 121° C. Final volume before start of dosage was around 360 liters. When this portion ran out, another similar portion was made. Total volume of pectin solution for one fermentation was around 725 liters.

After around 151 fermentation hours the fermentation process was stopped. The around 1850 liters of culture broth were cooled to around 5° C. and the enzymes were recovered according to the following method.

The culture broth was drum filtered on a vacuum drum filter (Dorr Oliver), which was precoated with Hyflo Super-Cell diatomaceous earth (filter aid). The filtrate was concentrated by evaporation to around 15% of the volume of the culture broth. The concentrate was filtered on a Seitz filter sheet (type supra 100) with 0.25% Hyflo Super-Cell as a filter aid (in the following table referred to as filtration I). The filtrate was precipitated with 561 g of $(NH_4)_2SO_4/l$ at a pH of 5.5, and 4% Hyflo Super-Cell diatomaceous earth is added as a filter aid. The precipitate and the filter aid are separated by filtration on a frame filter. The filter cake is dissolved in water, and insoluble parts are separated by filtration on a frame filter. The filtrate is check filtered on a Seitz filter sheet (type supra 100) with 0.25% Hyflo Super-Cell as a filter aid (in the following table referred to as filtration II). The filtrate is diafiltered on an ultrafiltration apparatus. After diafiltration the liquid is concentrated to a dry matter content of 12.7% (in the following table referred to as dry matter content in concentrate).

A facultative base treatment for partial removal of the protease activity can be carried out at this stage. In case the base treatment is used it is carried out at a pH of 9.2 for 1 hours, whereafter the pH value is adjusted to 5.0.

Now the liquid is check filtered and filtered for the purpose of germ reduction and the filtrate is freeze-dried on a freeze-drying equipment from Stokes.

The pure RGAE is obtainable from the A.a.e.p. as shown in Table 1.

TABLE 1

RHAMNOGALACTURONAN-ACETYL
ESTERASE PURIFICATION
*Aspergillus aculeatus* enzyme broth 1: ULTRAFILTRATION - DIALYSIS
Filtron Minisette, filter area 3500 cm², membrane NMWL 10,000
20 mM TRIS, pH 5.0; 5 × volume

2: IEC: WATER ACCELL QMA-PLUS, FIG. 1
(column: 5.0 × 23.0 cm, flow 60 ml/minute)
eluent = 20 mM TRIS, pH 5.0, increasin NaCl-gradient:
0.0M-linear-0.0125M-linear-0.25M-linear-0.5M

3: ULTRAFILTRATION - DIALYSIS
Filtron Minisette, filter area 3500 cm², membrane NMWL 10,000
20 nM TRIS, pH 4.2; 5 × volume

Figure 2:
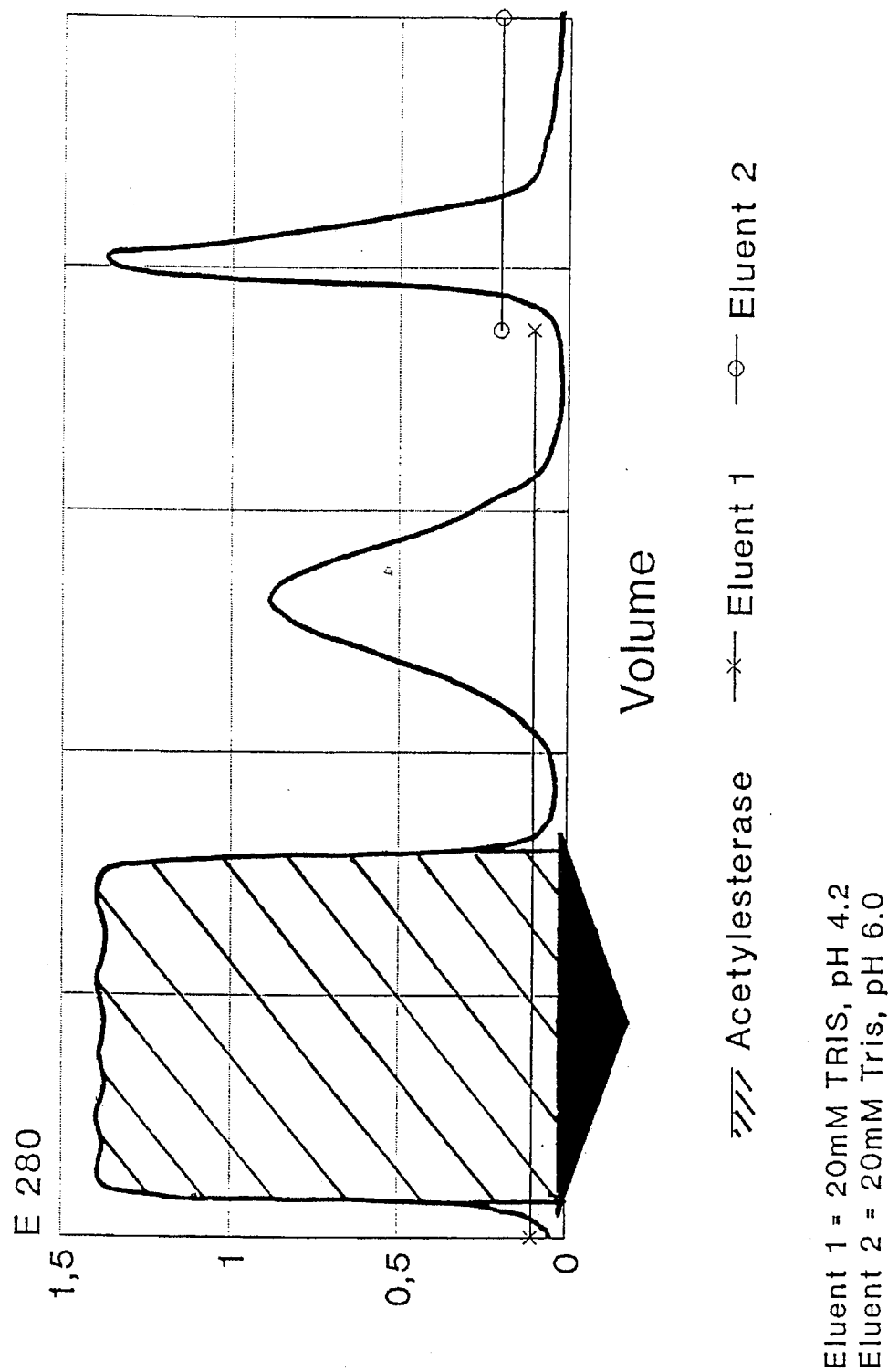
FIG. 2 shows an affinity chromatogram from which the non retained fraction was pooled (Eluent 1=20 mM TRIS pH 4.2; Eluent 2=20 mM TRIS pH 6.0;///rhamnogalacturonan acetyl esterase; —x— Eluent 1; —o— Eluent 2).

4: CROSSLINKED ALGINATE, FIG. 2
(column: 4.9 × 17.5 cm, flow 10 ml/minute)
eluent 1 = 20 mM TRIS, pH 4.2; eluent 2 = 20 mM TRIS, pH 6.0

5: SAMPLE PREPARATION
crosslinked alginate pool, addition of solid $(NH_4)_2SO_4$ to
2 M concentration and pH adjustment to 5.0

Figure 3:
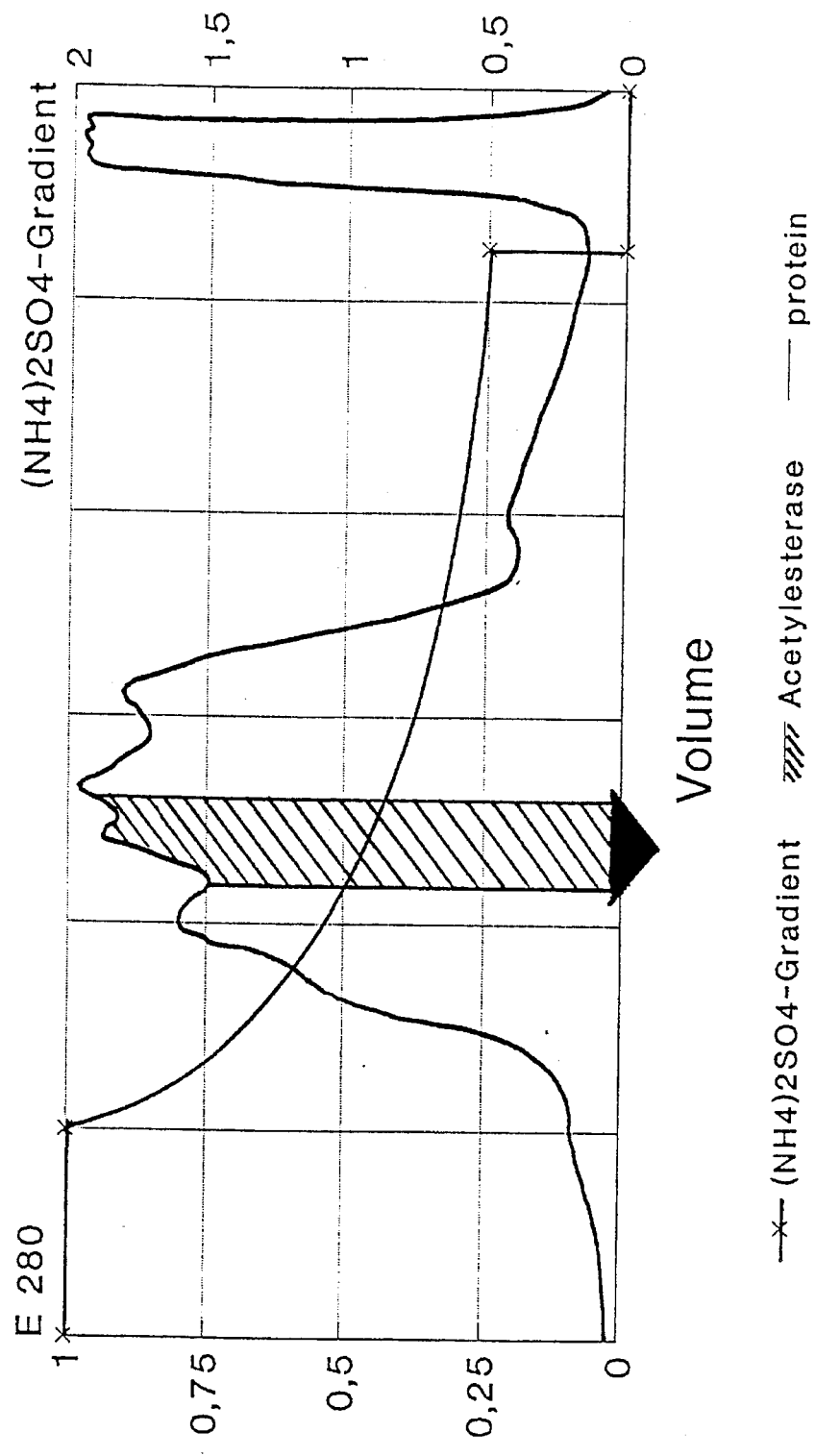
FIG. 3 shows a hydrophobic interaction chromatogram from which the rhamnogalacturon acetyl esterase fraction was pooled from 1.0–0.9M $(NH_4)_2SO_4$ (—x— $(NH_4)_2SO_4$ gradient;///rhamnogalacturonan acetyl esterase;—protein).

6: HIC: PHENYL TOYOPEARL 650 (M), FIG. 3
(column: 5.0 × 25.0 cm, flow 60 ml/minute)
eluent: water, decreasing $(NH_4)_2SO_4$-gradient:
2M-concave decrease
(=linear decrease of conductivity)-0.5M-step-0.0M

TABLE 1-continued

RHAMNOGALACTURONAN-ACETYL
ESTERASE PURIFICATION
*Aspergillus aculeatus* enzyme broth 7: ULTRAFILTRATION - DIALYSIS
Filtron Minisette, filter area 3500 cm², membrane NMWL 10,000

↓

Figure 4:
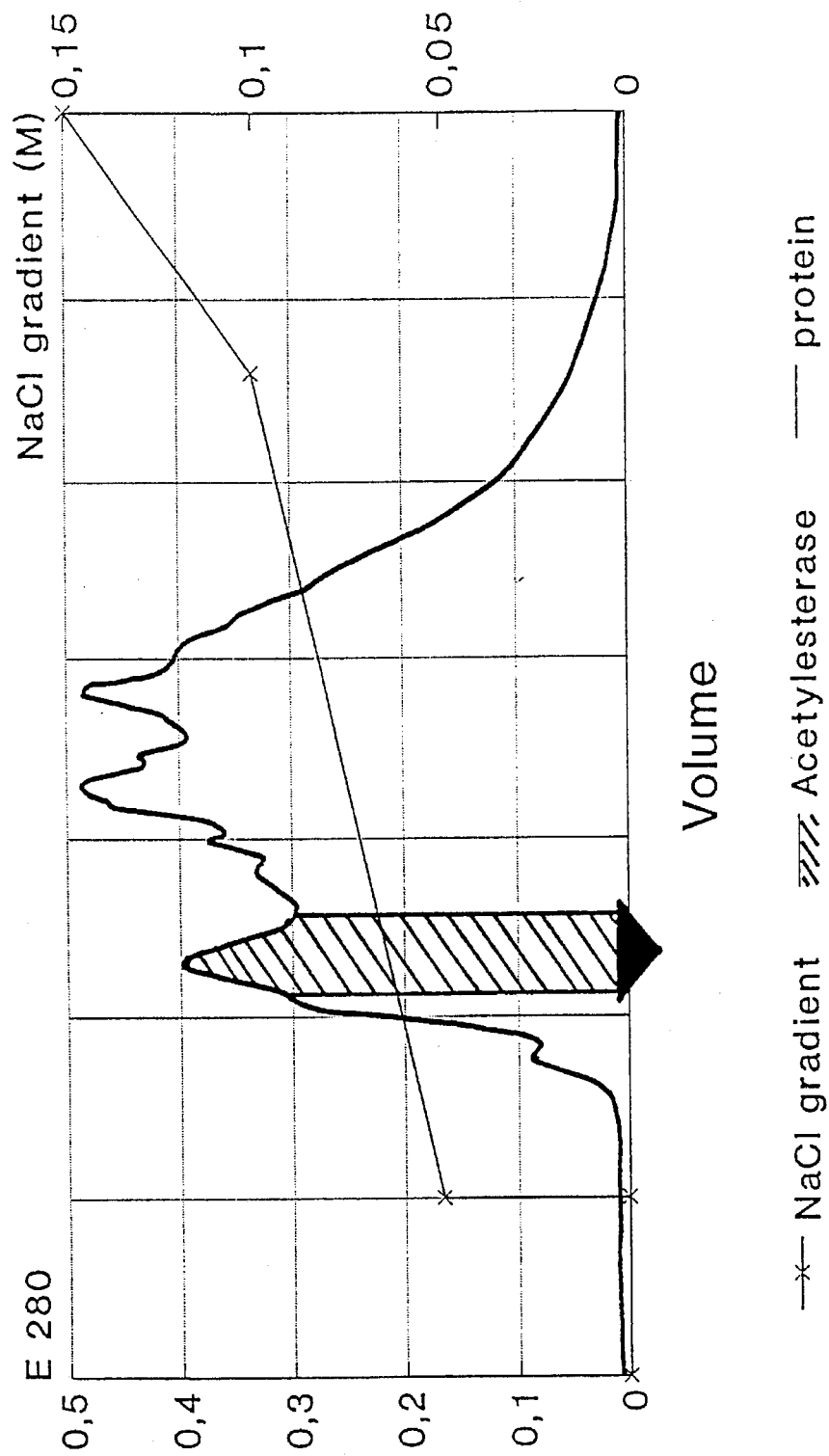
FIG. 4 shows an ion exchange chromatogram from which the rhamnogalacturonan acetyl esterase is pooled from 65–70 mM NaCl (—x— NaCl gradient (M); ///rhamnogalacturonan acetyl esterase;—protein).

8: IEC: PROTEIN PAC DEAE-8 HR, FIG. 4
(column. 2.0 × 10.0 cm, flow 4.5 ml/minute)
eluent: 20 mM TRIS, pH 5.0; increasing NaCl-gradient:

↓

9: SAMPLE PREPARATION
Protein Pac DEAE-8 HR pool,
dilution with 20 mM TRIS to 2 × volume
(decrease of NaCl-molarity for next step)

↓

Figure 5:
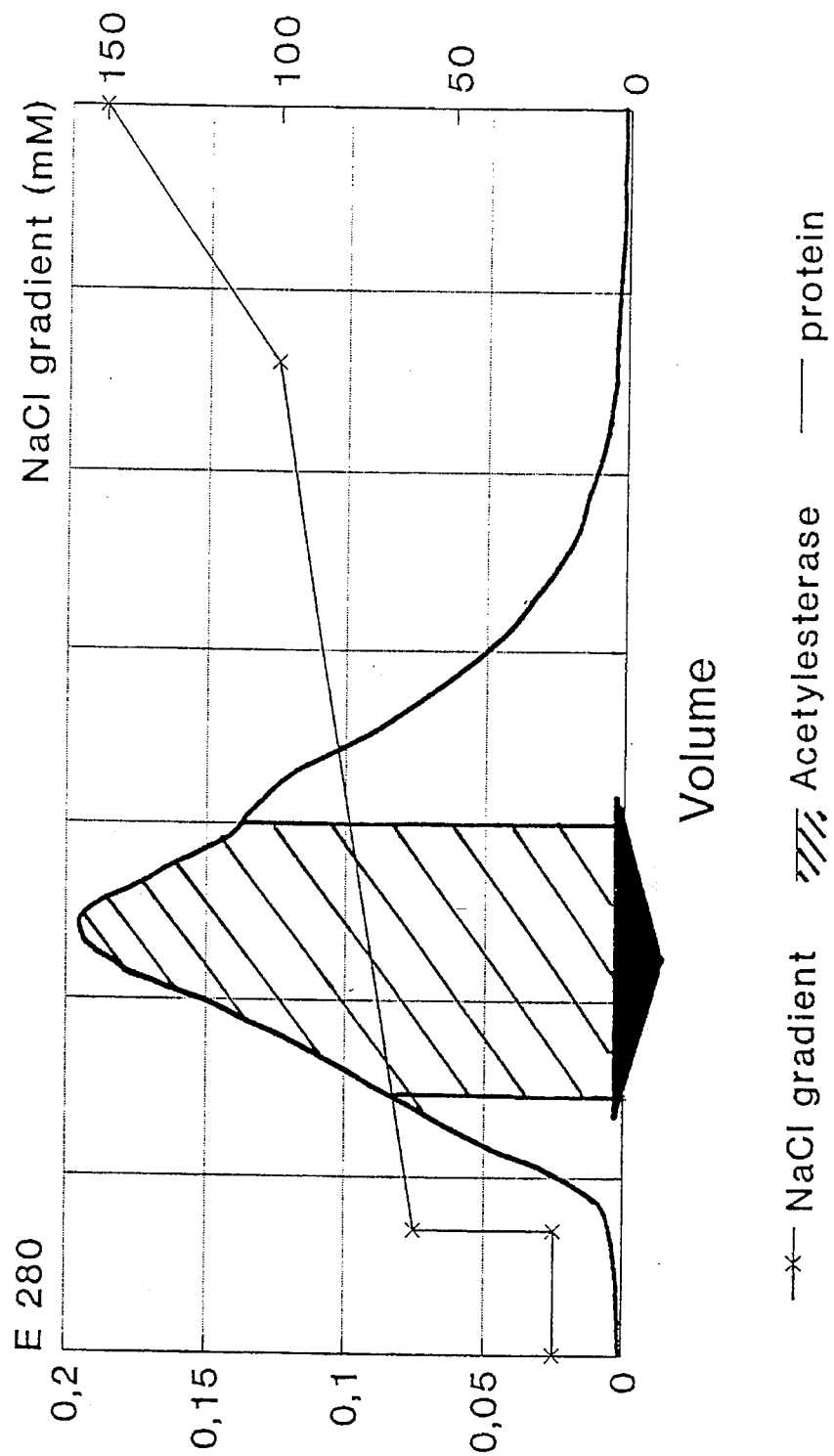
FIG. 5 shows an ion exchange chromatogram from which the rhamnogalacturonan acetyl esterase is pooled from 65–70 mM NaCl (—x— NaCl gradient (mM);///rhamnogalacturonan acetyl esterase;—protein).

10: IEC: PROTEIN PAC DEAE-8 HR, FIG. 5
(column: 2.0 × 10.0 cm, flow 4.5 ml/minute)
eluent: 20 mM TRIS, pH 5.0; increasing NaCl-gradient:
20 mM-step-60 mM-linear-100 mM-linear-150 mM

↓

RHAMNOGALACTURONAN-ACETYL ESTERASE ad 1:
Buffer exchange in order to prepare for step 2, removal of small particles and about 50% of the colour, dilution to max. 15 mg protein/ml (otherwise the sample will not bind to the column in step 2).

ad 2:
IEC is ion exchange chromatography. The acetylesterase fraction was pooled from 0.04–0.08M NaCl.

ad 3:
Concentration and buffer exchange in order to prepare for step 4.

ad 4:
Affinity chromatography—the non retained fraction was pooled. The preparation of the crosslinked alginate was done according to Rombouts F. M., C. C. J. M. Geraeds, J. Visser, W. Pilnik, "Purification of various pectic enzymes on crosslinked polyuronides", in: Gribnau, T. C. J., J. Visser, R. J. F. Nivard (Editors), Affinity Chromatography and Related Techniques, Elsevier Scientific Publishing Company, Amsterdam, 255–260, 1982.

ad 5:
Buffer adaption in order to prepare for step 6.

ad 6:
HIC is hydrophobic interaction chromatography. The acetyl esterase fraction was pooled from 1.0M–0.9M $(NH_4)_2SO_4$.

ad 7:
Concentration and buffer exchange in order to prepare for step 8.

ad 8:
IEC is ion exchange chromatography. The acetyl esterase fraction was pooled from 65 mM–70 mM NaCl.

ad 9:
Buffer adaption in order to prepare for step 10.

ad 10:
IEC is ion exchange chromatography. The acetyl esterase fraction was pooled from 65 mM–70 mM NaCl.

The thus purified RGAE may be employed for immunization of animals for the production of antibodies. More specifically, antiserum against the RGAE of the invention may be raised by immunizing rabbits (or other rodents) according to the procedure described by N. Axelsen et al. in: *A Manual of Quantitative Immunoelectrophoresis*, Blackwell Scientific Publications, 1973, Chapter 23, or A. Johnstone and R. Thorpe, *Immunochemistry in Practice*, Blackwell Scientific Publications, 1982 (more specifically pp. 27–31). Purified immunoglobulins may be obtained from the antisera, for example by salt precipitation $((NH_4)_2SO_4)$, followed by dialysis and ion exchange chromatography, e.g. on DEAE-Sephadex. Immunochemical characterization of proteins may be done either by Outchterlony double-diffusion analysis (O. Ouchterlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2,).

Amino acid sequence

The previously indicated partial amino acid sequence was determined from the purified RGAE by means of automated sequencing (Applied Biosystems 473A protein sequencer). On the basis of the sequence the purity of the sample is estimated to be more than 90%.

The RGAE is further characterized, as indicated in the following.

The RGAE has its optimal activity at pH 5.5 and at a temperature of 40° C. At 50° C. and pH 5.0 no activity loss could be observed within 20 hours. At 30° C. the pH-stability was highest at pH 6–7.

The RGAE has a specific activity towards MHR and released a maximum of about 70% of all acetyl groups present in MHR.

Combinations of this RGAE with pure pectin methylesterase of both citrus and fungal origin, pure exo- and endo-arabinases from *Aspergillus species* (*Aspergillus niger*, *Aspergillus aculeatus*) did not provide any increase in acetyl release from either beet pectin or apple MHR.

Pretreatment of these substrates, in order to remove arabinose side chains, did not exhibit any stimulating effect either. From these results it appears that a novel RGAE has been identified, which is highly specific for the acetyl esters of ramified pectic regions. Molecular weight: approx. 31,000 to 35,000 Daltons Isoelectric point: pH 4.2

A preferred embodiment of the RGAE according to the invention is characterized by the fact that the RGAE exhibits a pH-optimum of 4.0–7.0, preferably 4.5–6.0, an isoelectric point of 3.7–6.7, preferably 4.0–4.5, a molecular weight of between 30,000 and 50,000, and a temperature optimum between 10° and 50° C., preferably between 25° and 45° C.

Also the invention comprises a recombinant DNA sequence, which is characterized by encoding for the RGAE according to the invention.

A preferred embodiment of the recombinant DNA sequence according to the invention is characterized by the fact that it comprises a DNA sequence selected from a) the *Aspergillus aculeatus* RGAE DNA insert b) a DNA sequence which hybridizes to the coding region for the mature RGAE DNA comprised by the DNA insert of a) and which comprises a structural gene for a polypeptide with RGAE activity, and optionally a promoter, a coding region for a signal or leader peptide and/or transcriptional terminator.

c) a derivative of a DNA sequence defined in a) or b), or d) a DNA sequence which codes for a mature RGAE or a signal peptide or a leader peptide thereof and which is degenerate within the meaning of the genetic code with respect to a DNA sequence of a) or b).

A preferred embodiment of the recombinant DNA sequence according to the invention is characterized by the fact that it comprises the following partial DNA sequences

| | | | | | |
|---|---|---|---|---|---|
| a) | ATGAAGACCG | CCGCCTCTTG | CACCGCTCTT | CTTCCTCCCC | TCTGCCCTCG |
| | CCACGACNNG | (SEQ ID No. 2) | | | |
| b) | GTCTATCTCG | CGGGTGACTC | GACCATGGCC | AAGAATGGAG | GCGGGTCGGG |
| | AACTAACGGC | (SEQ ID No. 3) | | | |
| c) | TGGGGCGAGT | ACCTGCGAGT | TACCTCTCCG | CGACAGTGGT | TAACGACGCG |
| | GTCGCG | (SEQ ID No. 4) | | | |
| d) | GACGCAACCT | ATGAAGACCT | TGGAATGCCA | CCGTCAACTC | GTATTCCCCA |
| | TCGATCACAC | (SEQ ID No. 5) | | | |
| e) | CCACACCAGT | CCTGCGGCGC | GAGGTCGTGG | CTGAGCGTTC | TTGAAGGCGG |
| | TGGTATGCAC | (SEQ ID No. 6) | | | |
| f) | GGGTACGTCG | TTGAAGAGTG | TGTTGACGAC | GACGAGCTT | (SEQ ID No. 7) |

A preferred embodiment of the recombinant DNA sequence according to the invention is characterized by the fact that it comprises the following DNA sequences

| | | | | | |
|---|---|---|---|---|---|
| a) | ATGAAGACCG | CCGCCTCTTG | CACCGCTCTT | CTTCCTCCCC | TCTGCCCTCG |
| | CCACGACNNG | GTCTATCTCG | CGGGTGACTC | GACCATGGCC | AAGAATGGAG |
| | GCGGGTCGGG | AACTAACGGC | TGGGGCGAGT | ACCTGCGAGT | TACCTCTCCG |
| | CGACAGTGGT | TAACGACGCG | GTCGCG | (SEQ ID No. 8) | |
| b) | GACGCAACCT | ATGAAGACCT | TGGAATGCCA | CCGTCAACTC | GTATTCCCCA |
| | TCGATCACAC | CCACACCAGT | CCTGCGGCGC | GAGGTCGTGG | CTGAGCGTTC |
| | TTGAAGGCGG | TGGTATGCAC | GGGTACGTCG | TTGAAGAGTG | TGTTGACGAC |
| | GACGAGCTT | | | (SEQ ID No. 9) | |

A preferred embodiment of the recombinant DNA sequence according to the invention is characterized by the fact that it comprises

| | | | | |
|---|---|---|---|---|
| AGTCTATAAG | AAGATTGACA | GCCAAGAACA | CCACCCACAA | TGAAGACCGC |
| CGCCTCTTGC | ACCGCTCTTC | TTCCTCCCCT | CTGCCCTCGC | CACGACNNGG |
| TCTATCTCGC | GGGTGACTCG | ACCATGGCCA | AGAATGGAGG | CGGGTCGGGA |
| ACTAACGGCT | GGGGCGAGTA | CCTCGCCAGT | TACCTCTCCG | CGACAGTGGT |
| TAACGACGCG | GTCGCGGGCC | GCAGCGCGCG | CTCGTACACA | CGCGAGGGTC |
| GGTTCGAGAA | CATCGCCGAT | GTAGTGACGG | CGGGCGACTA | CGTGATCGTC |
| GAGTTCGGCC | ACAACGACGG | TGGCTCGCTG | TCCACGGACA | ATGGACGCAC |
| CGACTGCTCC | GGTACCGGGG | CAGAAGTCTG | CTATAGCGTC | TACGACGGGG |
| TCAACGAGAC | CATCCTCACC | TTCCCCGCCT | ACCTGGAGAA | CGCCGCCAAG |
| CTGTTCACCG | CCAAGGGCGC | CAAGGTCATT | CTCAGCAGCC | AGACCCCCAA |
| CAACCCCTGG | GAGACCGGCA | CCTTCGTCAA | CTCCCCCACG | CGCTTCGTTG |
| AGTACGCCGA | GCTGGCCGCC | GAGGTCGCTG | GCGTCGAGTA | CGTCGACCAC |
| TGGTCCTACG | TGGACAGCAT | CTATGAGACC | TTGGCAATGC | CACCGTCAAC |
| TCGTATTCCC | CATCGATCAC | ACCCACACCA | GTCCTGCGGC | GCGAGGTCGT |
| GGCTGAGCGT | TCTTGAAGGC | GGTGGTATGC | ACGGGTACGT | CGTTGAAGAG |
| TGTGTTGACG | ACGACGAGCT | TTGAGGGGAC | ATGTCTGTGA | TTGAGCAGAT |
| GGAAAGACAA | AGGAGTGGAC | GGATAAGGAC | AGGAGTTGTC | ATGTATAGTG |
| GTAGTTTGTG | CATTGCAAAT | GGTATCTGAA | CTGGCTCGCT | TATGCTCATG |
| ATCGACAAAA | AAAAAAAAAA | AAAAAAAAAA | AAAAA | (SEQ ID NO. 10) | or a sequence homologous thereto encoding for an RGAE according to the invention.

Also, the invention comprises a vector which is characterized by the fact that it comprises the recombinant DNA sequence according to the invention.

A preferred embodiment of the vector according to the invention is characterized by the fact that the promoter is the *Aspergillus oryzae* takaamylase promoter.

Also the invention comprises a transformed host which is characterized by the fact that it contains the vector according to the invention.

A preferred embodiment of the transformed host according to the invention is characterized by the fact that the transformed host is an Aspergillus strain. Hereby a good production capacity of the RGAE is obtained.

A preferred embodiment of the transformed host according to the invention is characterized by the fact that the transformed host is a strain belonging to the species *Aspergillus aculeatus, Aspergillus niger, Aspergillus oryzae* or *Aspergillus awamori*. Hereby a good production capacity of the RGAE is obtained.

A preferred embodiment of the transformed host according to the invention is characterized by the fact that the transformed host is a microorganism, which in its non-transformed condition does not produce RGAE or only produces RGAE in insignificant amounts, preferably Bacillus sp., *E. coil* or *S. cerevisiae*. Hereby a "tailor made" enzyme preparation with high RGAE activity and a spectrum of other wanted specific enzyme activities can be obtained.

Also, the invention comprises a method for production of an RGAE by use of a transformed host according to the invention. By means of this method the RGAE can be obtained in high yield.

Also, the invention comprises the RGAE, when produced by the method according to the invention. RGAE can be obtained in high yield.

Also, the invention comprises an enzyme preparation which is characterized by the fact that it contains a pectinase preparation usable for degradation or modification of plant cell walls enriched with the RGAE according to the invention. In this manner a boosting of the cell wall degrading ability of the pectinase preparation can be obtained.

A preferred embodiment of the enzyme preparation according to the invention is characterized by the fact that the pectinase preparation is producible by means of a microorganism belonging to the genus Aspergillus, preferably *Aspergillus niger, Aspergillus aculeatus, Aspergillus awamori* or *Aspergillus oryzae*. Such preparation is able to provide an extraordinary good decomposition of vegetable cell walls.

A preferred embodiment of the enzyme preparation according to the invention is characterized by the fact that the RGAE is the RGAE produced by means of the method according to the invention. The production costs of this preparation are relatively low.

Also, the invention comprises a use of the RGAE according to the invention as an agent for degradation or modification of acetylated rhamnogalacturonan.

A preferred embodiment of the use of the RGAE according to the invention is a use as an agent for degradation or modification of plant cell walls. At present, degradation of plant cell walls is the most preferred use of the RGAE according to the invention, due to the high plant cell wall degradation activity.

A preferred embodiment of the use of the RGAE according to the invention is a use where the RGAE is used together with enzymes specific to deacylated or partially deacylated MHR. These further enzymes include all enzymes, which attack deacetylated and partially deacetylated ramified rhmanogalacturonans with a higher specificity than they attack acetylated rhamnogalacturonans, including enzymes which attack the rhmanogalacturonan backbone by endo or exo attack, or enzymes which attack the side branches.

Also the invention comprises a use of the enzyme preparation according to the invention as an agent for degradation or modification of acetylated rhamnogalacturonanes.

A preferred embodiment of the use of the enzyme preparation according to the invention is a use as an agent for degradation or modification of plant cell walls. At present, degradation of plant cell walls is the most preferred use of the enzyme preparation according to the invention, due to the high plant cell wall degradation activity.

A preferred embodiment of the use of the enzyme preparation according to the invention is a use where the enzyme preparation is used together with enzymes specific to deacylated or partially deacylated MHR. These further enzymes include all enzymes, which attack deacetylated and partially deacetylated ramified rhmanogalacturonans with a higher specificity than they attack acetylated rhamnogalacturonans, including enzymes which attack the rhmanogalacturonan backbone by endo or exo attack, or enzymes which attack the side branches.

Figure 6:
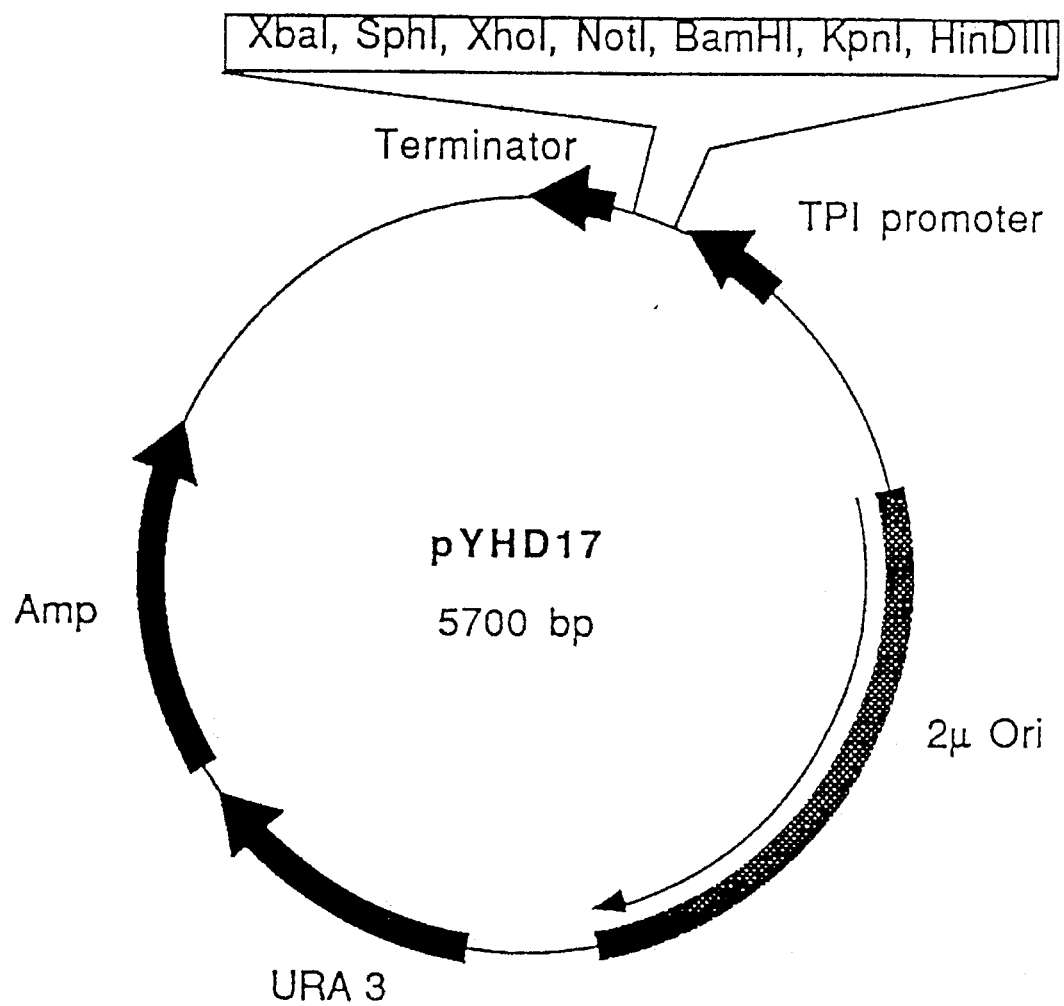
FIG. 6 shows the expression plasmid pYHD 17.

FIG. 6 is a map of plasmid pYHD17, wherein "TPI promoter" indicates the *S. cerevisiae* triose phosphate isomerase promoter, "Terminator" indicates the transcription terminator, "Amp" indicates the gene mediating ampicillin resistance, "2µ ori" indicates the yeast plasmid 2µ origin of replication, and "URA3" indicates a gene encoding a selection marker complementing a uracil deficiency in the host strain.

EXAMPLES

Materials and Methods

Donor organism: mRNA was isolated from *Aspergillus aculeatus*, CBS 101.43, grown in a soy-containing fermentation medium with agitation to ensure sufficient aeration. Mycelia were harvested after 3–5 days' growth, immediately frozen in liquid nitrogen and stored at −80° C.

Yeast strains: The *Saccharomyces cerevisiae* strain used was yNG231 (MAT alpha, leu2, ura3-52, his4-539, pep4-delta 1, cir+) or JG169 (MATα; ura 3-52; leu 2-3, 112; his 3-D200; pep 4-113; prc1::HIS3; prb1::LEU2; cir+).

Construction of an Expression Plasmid

The commercially available plasmid pYES II (Invitrogen) was cut with SpeI, filled in with Klenow DNA polymerase+ dNTP and cut with ClaI. The DNA was size fractionated on an agarose gel, and a fragment of about 2000 bp was purified by electroelution. The same plasmid was cut with ClaI/ PvuII, and a fragment of about is 3400 bp was purified by electroelution. The two fragments were ligated to a blunt-ended SphI/EcoRI fragment containing the yeast TPI promoter. This fragment was isolated from a plasmid in which the TPI promoter from *S. cerevisiae* (cf. T. Albers and G. Kawasaki, *J. Mol. Appl. Genet.* 1, 1982, pp. 41 9–434) was slightly modified: an internal SphI site was removed by deleting the four bp constituting the core of this site. Furthermore, redundant sequences upstream of the promoter were removed by Bal1 exonuclease treatment followed by addition of a SphI linker. Finally, an EcoRI linker was added at position −10. After these modifications, the promoter is included in a SphI-EcoRI fragment. Its effeciency compared to the original promoter appears to be unaffected by the modifications. The resulting plasmid pYHD17 is shown in FIG. 6.

Preparation of RNase-free glassware, tips and solutions

All glassware used in RNA isolations was baked at +220° C. for at least 12 h. Eppendorf tubes, pipet tips and plastic columns were treated in 0.1% diethylpyrocarbonate (DEPC) in EtOH for 12 hours, and autoclaved. All buffers and water (except Tris-containing buffers) were treated with 0.1% DEPC for 12 hours at 37° C., and autoclaved.

Extraction of total RNA

The total RNA was prepared by extraction with guanidinium thiocyanate followed by ultracentrifugation through a 5.7M CsCl cushion (Chirgwin et al., 1979) using the following modifications. The frozen mycelia were ground in liquid $N_2$ to fine powder with a mortar and a pestle, followed by grinding in a precooled coffee mill, and immediately suspended in 5 vols of RNA extraction buffer (4M GuSCN, 0.5% Na-laurylsarcosine, 25 mM Na-citrate, pH 7.0, 0.1M β-mercaptoethanol). The mixture was stirred for 30 minutes at RT° and centrifuged (30 minutes, 5000 rpm, RT°, Heraeus Megafuge 1.0 R) to pellet the cell debris. The supernatant was collected, carefully layered onto a 5.7M CsCl cushion (5.7M CsCl, 0.1M EDTA, pH 7.5, 0.1% DEPC; autoclaved prior to use) using 26.5 ml supernatant per 12.0 ml CsCl cushion, and centrifuged to obtain the total RNA (Beckman, SW 28 rotor, 25,000 rpm, RT°, 24 h). After centrifugation the supernatant was carefully removed and the bottom of the tube containing the RNA pellet was cut off and rinsed with 70% EtOH. The total RNA pellet was transferred into an Eppendorf tube, suspended in 500 µl TE, pH 7.6 (if difficult, heat occasionally for 5 minutes at 65° C.), phenol extracted and precipitated with ethanol for 12 hours at −20° C. (2.5 vols EtOH, 0.1 vol 3M NaAc, pH 5.2). The RNA was collected by centrifugation, washed in 70% EtOH, and resuspended in a minimum volume of DEPC-DIW. The RNA concentration was determined by measuring $OD_{260/280}$.

Isolation of poly(A)+RNA

The poly(A)+ RNAs were isolated by oligo(dT)-cellulose affinity chromatography (Aviv & Leder, 1972). Typically, 0.2 g of oligo(dT) cellulose (Boehringer Mannheim) was preswollen in 10 ml of 1×column loading buffer (20 mM Tris-Cl, pH 7.6, 0.5M NaCl, 1 mM EDTA, 0.1% SDS), loaded onto a DEPC-treated, plugged plastic column (Poly Prep Chromatography Column, Bio Rad), and equilibrated with 20 ml 1×loading buffer. The total RNA was heated at 65° C. for 8 minutes, quenched on ice for 5 minutes, and after addition of 1 vol 2×column loading buffer to the RNA sample loaded onto the column. The eluate was collected and reloaded 2–3 times by heating the sample as above and quenching on ice prior to each loading. The oligo(dT) column was washed with 10 vols of 1×loading buffer, then with 3 vols of medium salt buffer (20 mM Tris-Cl, pH 7.6, 0.1M NaCl, 1 mM EDTA, 0.1% SDS), followed by elution of the poly(A)+ RNA with 3 vols of elution buffer (10 mM Tris-Cl, pH 7.6, 1 mM EDTA, 0.05% SDS) preheated to +65° C., by collecting 500 µl fractions. The $OD_{260}$ was read for each collected fraction, and the mRNA containing fractions were pooled and ethanol precipitated at –20° C. for 12 h. The poly(A)+ RNA was collected by centrifugation, resuspended in DEPC-DIW and stored in 5–10 µg aliquots at –80° C.

Northern blot analysis

The poly(A)+ RNAs (5 µg/sample) from various mycelia were electrophoresed in 1.2 agarose-2.2M formaldehyde gels (Sambrook et al., 1989) and blotted to nylon membranes (Hybond-N, Amersham) with 10×SSC (Sambrook et al., 1989) as transfer buffer. Three random-primed (Feinberg & Vogelstein, 1983) $^{32}$P-labeled cDNA probes were used in individual hybridizations: 1) a 1.3 kb Not I-Spe I fragment for polygalacturonase I from A. aculeatus, 2) a 1.3 kb Not I-Spe I fragment encoding endoglucanase I from A. aculeatus and 3) a 1.2 kb Eag I fragment for galactanase I from A. aculeatus. Northern hybridizations were carried out in 5×SSC (Sambrook et al., 1989), 5×Denhardt's solution (Sambrook et al., 1989), 0.5% SDS (w/v) and 100 µg/ml denatured salmon sperm DNA with a probe concentration of ca. 2 ng/ml for 16 hours at 65° C. followed by washes in 5×SSC at 65° C. (2×15 minutes), 2×SSC, 0.5% SDS (1×30 minutes), 0.2×SSC, 0.5% SDS (1×30 minutes), and 5×SSC (2×15 minutes). After autoradiography at –80° C. for 12 hours, the probe #1 was removed from the filter according to the manufacturer's instructions and rehybridized with probe #2, and eventually with probe #3. The RNA ladder from Bethesda Research Laboratories was used as a size marker. cDNA synthesis:

First strand synthesis

Double-stranded cDNA was synthesized from 5 µg of A. aculeatus poly(A)+ RNA by the RNase H method (Gubler & Hoffman 1983, Sambrook et al., 1989) using the hair-pin modification. The poly(A)+ RNA (5 µg in 5 µl of DEPC-treated water) was heated at 70° C. for 8 minutes, quenched on ice, and combined in a final volume of 50 µl with reverse transcriptase buffer (50 mM Tris-Cl, pH 8.3, 75 mM KCl, 3 mM MgCl2, 10 mM DTT, Bethesda Research Laboratories) containing 1 mM each dNTP (Pharmacia), 40 units of human placental ribonuclease inhibitor (RNasin, Promega), 10 µg of oligo(dT)$_{12-18}$ primer (Pharmacia) and 1000 units of SuperScript II RNase H-reverse transcriptase (Bethesda Research Laboratories). First-strand cDNA was synthesized by incubating the reaction mixture at 45° C. for 1 hour.

Second strand synthesis

After synthesis 30 µl of 10 mM Tris-Cl, pH 7.5, 1 mM EDTA was added, and the mRNA:cDNA hybrids were ethanol precipitated for 12 hours at –20° C. by addition of 40 µg glycogen carrier (Boehringer Mannheim) 0.2 vols 10 M NH$_4$Ac and 2.5 vols 96% EtOH. The hybrids were recovered by centrifugation, washed in 70% EtOH, air dried and resuspended in 250 µl of second strand buffer (20 mM Tris-Cl, pH 7.4, 90 mM KCl, 4.6 mM MgCl2, 10 mM (NH$_4$)$_2$SO$_4$, 16 µM βNAD$^+$) containing 100 µM each dNTP, 44 units of E. coil DNA polymerase I (Amersham), 6.25 units of RNase H (Bethesda Research Laboratories) and 10.5 units of E. coil DNA ligase (New England Biolabs). Second strand cDNA synthesis was performed by incubating the reaction tube at 16° C. for 3 hours, and the reaction was stopped by addition of EDTA to 20 mM final concentration followed by phenol extraction.

Mung bean nuclease treatment

The double-stranded (ds) cDNA was ethanol precipitated at –20° C. for 12 hours by addition of 2 vols of 96% EtOH, 0.1 vol 3M NaAc, pH 5.2, recovered by centrifugation, washed in 70% EtOH, dried (SpeedVac), and resuspended in 30 µl of Mung bean nuclease buffer (30 mM NaAc, pH 4.6, 300 mM NaCl, 1 mM ZnSO4, 0.35 mM DTT, 2% glycerol) containing 36 units of Mung bean nuclease (Bethesda Research Laboratories). The single-stranded hair-pin DNA was clipped by incubating the reaction at 30° C. for 30 minutes, followed by addition of 70 µl 10 mM Tris-Cl, pH 7.5, 1 mM EDTA, phenol extraction, and ethanol precipitation with 2 vols of 96% EtOH and 0.1 vol 3M NaAc, pH 5.2 at –20° C. for 12 hours.

Blunt-ending with T4 DNA polymerase

The ds cDNA was blunt-ended with T4 DNA polymerase in 50 µl of T4 DNA polymerase buffer (20 mM Tris-acetate, pH 7.9, 10 mM MgAc, 50 mM KAc, 1 mM DTT) containing 0.5 mM each dNTP and 7.5 units of T4 DNA polymerase (Invitrogen) by incubating the reaction mixture at +37° C. for 15 minutes. The reaction was stopped by addition of EDTA to 20 mM final concentration, followed by phenol extraction and ethanol precipitation.

Adaptor ligation and size selection

After the fill-in reaction the cDNA was ligated to non-palindromic BstX I adaptors (1 µg/µl, Invitrogen) in 30 µl of ligation buffer (50 mM Tris-Cl, pH 7.8, 10 mM MgCl2, 10 mM DTT, 1 mM ATP, 25 µg/ml bovine serum albumin) containing 600 pmol BstX I adaptors and 5 units of T4 ligase (Invitrogen) by incubating the reaction mix at +16° C. for 12 hours. The reaction was stopped by heating at +70° C. for 5 minutes, and the adapted cDNA was size-fractionated by agarose gel electrophoresis (0.8% HSB-agarose, FMC) to separate unligated adaptors and small cDNAs. The cDNA was size-selected with a cut-off at 0.7 kb, and the cDNA was electroeluted from the agarose gel in 10 mM Tris-Cl, pH 7.5, 1 mM EDTA for 1 hour at 100 volts, phenol extracted and ethanol precipitated at –20° C. for 12 hours as above.

Construction of cDNA libraries:

The adapted, ds cDNA was recovered by centrifugation, washed in 70% EtOH and resuspended in 25 ml DIW. Prior to large-scale library ligation, four test ligations were carried out in 10 µl of ligation buffer (same as above) each containing 1 ||l ds cDNA (reaction tubes #1–#3), 2 units of T4 ligase (Invitrogen) and 50 ng (tube #1), 100 ng (tube #2) and 200 ng (tubes #3 and #4) Bst XI cleaved yeast expression vector either pYES 2.0 vector Invitrogen or yHD13). The ligation reactions were performed by incubation at +16° C. for 12 hours, heated at 70° C. for 5 minutes, and 1 µl of each ligation electroporated (200Ω, 2.5 kV, 25 µF) to 40 µl competent E. coli 1061 cells (OD600=0.9 in 1 liter LB-broth, washed twice in cold DIW, once in 20 ml of 10% glycerol, resuspended in 2 ml 10% glycerol). After addition of 1 ml SOC to each transformation mix, the cells were grown at +37° C. for 1 hour, 50 µl plated on LB+ampicillin plates (100 µg/ml) and grown at +37° C. for 12 hours.

Using the optimal conditions a large-scale ligation was set up in 40 µl of ligation buffer containing 9 units of T4 ligase, and the reaction was incubated at +16° C. for 12 hours. The ligation reaction was stopped by heating at 70° C. for 5 minutes, ethanol precipitated at −20° C. for 12 hours, recovered by centrifugation and resuspended in 10 µl DIW. One µl aliquots were transformed into electrocompetent E. coil 1061 cells using the same electroporation conditions as above, and the transformed cells were titered and the library plated on LB+ampicillin plates with 5000–7000 c.f.u./plate. To each plate was added 3 ml of medium. The bacteria were scraped off, 1 ml glycerol was added and stored at −80° C. as pools. The remaining 2 ml were used for DNA isolation. If the amount of DNA was insufficient to give the required number of yeast transformants, large scale DNA was prepared from 500 ml medium (TB) inoculated with 50 µl of −80° C. bacterial stock propagated overnight.

Generation of a cDNA probe by polymerase chain reaction

To obtain a cDNA probe for rhamnogalacturonan acetylesterase I from A. aculeatus RE4, a degenerate oligonucleotide (RGAE/s$_2$, FIG. 7) corresponding to a region in the NH$_2$-terminal sequence of the purified enzyme was synthesized by incorporating deoxyinosines at four of the ambiguous positions. FIG. 7 shows the deduced, deoxyinosine-containing primer sequence used in the PCR aligned with the corresponding amino acid sequence (SEQ ID NO:13) obtained from purified rhamnogalacturonan acetylesterese I from Aspergillus aculeatus. The primer was used in conjunction with the direct (primer #22, 5'-CTGTAATACGACT-CACTA-3') (SEQ ID NO:11) and reverse (primer #43, 5'-ATTACATGATGCGGCCCT-3') (SEQ ID NO:12) pYES 2.0 primers to amplify the target RGAEse cDNA from an amplified cDNA library pool containing 7000 clones employing the polymerase chain reaction technique (Ohara et al. 1989). The PCR reactions were carried out in 100 µl PCR buffer (10 mM Tris-HCl, pH 8.3, 50 mM KCl, 1.5 mM MgCl$_2$, 0.01%, Perkin-Elmer, Cetus) containing 550 pmol of sense primer (RGAE/s$_2$) and 800 pmol of each antisense primer (see above), 1 µg template DNA (Qiagen-purified plasmid DNA from cDNA library pool #33) and 200 µM each dNTP using a DNA thermal cycler and 2.5 units of Taq polymerase (Perkin-Elmer, Cetus). Thirty cycles of PCR were performed using a cycle profile of denaturation at 94° C. for 1 minute, annealing at 55° C. for 2 minutes, and extension at 72° C. for 3 minutes.

Twenty µl aliquots of the amplification products were analyzed by electrophoresis on 0.7% agarose gels revealing a 0.9 kb major product with one primer pair (sense, RGAE/s$_2$; antisense, pYES 2.0 reverse primer #43). The DNA fragment of interest was excised from the gel, recovered by electroelution (Sambrook et al. 1989) using type D-0405 seamless dialysis tubing (Sigma), followed by phenol extraction and ethanol precipitation at −20° C. for 12 hours. The PCR product was blunt-ended at 37° C. for 10 minutes in 20 pl buffer (20 mM Tris-acetate, pH 7.9, 10 mM MgAc, 50 mM KAc, 1 mM DTT) containing 50 pM each dNTP and 3 units of T4 DNA polymerase (New England Biolabs). The reaction was stopped by incubation at 70° C. for 5 minutes, chilled on ice for 5 minutes and diluted in 50 µl of kinase buffer (70 mM Tris-HCl, pH 7.6, 10 mM MgCl$_2$, 5 mM DTT) followed by phosphorylation at 37° C. for 30 minutes with T4 polynucleotide kinase (10 U, New England Biolabs) and 1 mM ATP pH 7.0 (Pharmacia), phenol extraction, ethanol precipitation and ligation at 16° C. for 12 hours into Sma I-cut, dephosphorylated pUC18 vector (50 ng per ligation, Pharmacia).

E. coil DH5α was transformed to ampicillin resistance (Hanahan 1985) using 5 µl of the ligation mixture, and 13 clones were analyzed by isolation of plasmid miniprep. DNA (Sambrook et al. 1989), and EcoRI/HindIII digestion of the plasmid subclones, followed by sequencing the ends of the 0.9 kb insert from one subclone (pRGA19) with universal pUC primers (Sanger et al. 1977). Nucleotide sequence analysis of the pRGA 19 subclone revealed a unique open reading frame which, in addition to the primer encoded amino acids, contained 10 additional residues concurring with the available NH=-terminal sequence from the purified enzyme, thus confirming that the PCR had specifically amplified the desired region of the rhamnogalacturonan acetylesterase I cDNA (FIG. 8) (SEQ ID NO:15) and (SEQ ID NO:16). FIG. 8 shows the nucleotide sequence of the 5'-end of the rgal cDNA, and the deduced primary structure of RGAEase I from A. aculeatus. The NH$_2$-terminal signal peptide preceding the mature protein is underlined.

Southern blot analysis

Qiagen purified DNA (3 µg) from eight individual cDNA library pools (#33, 90, 100, 130, 136, 140, 142, 148) was digested to completion with Eag I (3 U/µg DNA, New England Biolabs), fractionated on a 0.7% agarose gel, denatured and blotted to a nylon filter (Hybond-N, Amersham) using 10×SSC (Sambrook et al. 1989) as transfer buffer (Southern 1975). The purified 0.9 kb RGAEse I PCR fragment was $^{32}$P-labeled (>1×10$^9$ cpm/µg) by random-priming (Feinberg & Vogelstein 1983) and used as a probe in Southern analysis. The hybridization was carried out in 2×SSC (Sambrook et al. 1989), 5×Denhardt's solution (Sambrook et al. 1989), 1% (w/v) SDS and 100 µg/ml denatured salmon sperm DNA with a probe concentration of 2.5 ng/ml for 16 hours at 65° C. followed by washes in 2×SSC (2×15 minutes), 2×SSC, 1% SDS at 65° C. for 30 minutes, then in 0.2×SSC, 1% SDS at 65° C. for 30 minutes, and finally in 2×SSC (2×15 minutes). The filter was autoradiographed at −80° C. for 12 hours oursrevealing a single strongly hybridising 1.0 kb fragment in each cDNA pool. This indicated that each analyzed pool contained a full-length cDNA copy encoding RGAEse I from A. aculeatus. Therefore, pool #33 was chosen for further experiments.

Northern blot analysis

To estimate the steady-state levels of the A. aculeatus RGAEse I mRNA during growth in the RS3 medium, poly(A)$^+$ RNA was isolated from mycelia haNested daily after 1–5 days growth in the above medium, and subjected to Northern analysis. The poly(A)+RNAs (5 µg/sample) were electrophoresed in 1.2 agarose-2.2M formaldehyde gels (Sambrook et al., 1989) and blotted to a nylon membrane (Hybond-N, Amersham) with 10×SSC (Sambrook et al., 1989) as transfer buffer. The RNA ladder from Bethesda Research Laboratories was used as a size marker, and a random-primed (Feinberg & Vogelstein, 1983) $^{32}$P-labeled 0.9 kb RGAEse I PCR product (see previous section) as a probe in the Northern analysis. The hybridization was carried out in 5×SSC (Sambrook et al., 1989), 5×Denhardt's solution (Sambrook et al., 1989), 0.5% SDS (w/v) and 100 µg/ml denatured salmon sperm DNA with a probe concentration of ca. 2.5 ng/ml for 16 hours at 65° C. followed by washes in 5×SSC at 65° C. (2×15 minutes), 2×SSC, 0.5% SDS (1×30 minutes), 0.2×SSC, 0.5% SDS (1×30 minutes), and 5×SSC (2×15 minutes). The filter was autoradiographed at −80° C. for 4 days.

The RGAEse I cDNA probe detects a 1.0 kb mRNA species readily in 5-day-old mycelia, and weakly in 4-dayold mycelia but not in 1 to 3-day-old mycelia coinciding with the decreasing levels of glucose in the growth medium after day 1, with no detectable glucose in the supernatant after day 3.

Isolation and characterization of a full-length cDNA encoding rhamnogalacturonan acetylesterase I (RGAEse I) from *A. aculeatus*

To isolate a full-length cDNA clone for RGAEse I, 30 000 colonies from the cDNA library pool #33 were plated on LB-agar (24×24 cm plate, Nunc) containing ampicillin (100 µg/ml) and replicated on an LB+amp-plate covered with a nylon filter (Hybond-N, Amersham). The purified 0.9 kb RGAEse I PCR fragment was 32P-labeled by random-priming as above, and used as a probe in screening the library pool by colony hybridization (Sambrook et al., 1989). The hybridization was carried out in 2×SSC (Sambrook et al., 1989), 5×Denhardt's solution (Sambrook et al. 1989), 1% (w/v) SDS and 100 µg/ml denatured salmon sperm DNA with a probe concentration of 2.5 ng/ml for 16 hours at 65° C., then in 2×SSC (2×15 minutes), 0.2×SSC, 1% SDS (2×30 minutes), and in 2×SSC (2×15 minutes) followed by autoradiography at −80° C. for 12 hours. Screening of 30,000 colonies from pool 33 yielded 5 putative RGAEse I cDNA clones that were colony-purified by two more rounds of hybridizations. One of these clones (designated pRGA1) was characterized by digesting the plasmid with HindIII and Xbal and sequencing the ends of the 1.0 kb cDNA insert with forward and reverse pYES 2.0 polylinker primers.

The 1.0 kb insert in pRGA1 contains a 0.85 kb open reading frame (ORF) initiating with an ATG codon at nucleotide position 40 and terminating with a TGA stop codon (FIGS. 8 and 9). FIG. 9 (SEQ ID NO:17) and (SEQ ID NO:18) shows the nucleotide sequence of the 3'-end of the rga1 cDNA and the deduced primary structure of RGAEase I from *A. aculeatus*. The ORF is preceded by a 39 bp 5' non-coding region and followed by a 132 bp 3' non-coding region and a poly(A) tail. Comparison of the deduced protein sequence with the NH2-terminal sequence of the purified mature RGAEse I reveals that the cDNA encodes a precursor protein containing a 18 residue signal peptide (FIG. 8).

Construction of an Aspergillus expression vector

Figure 10:
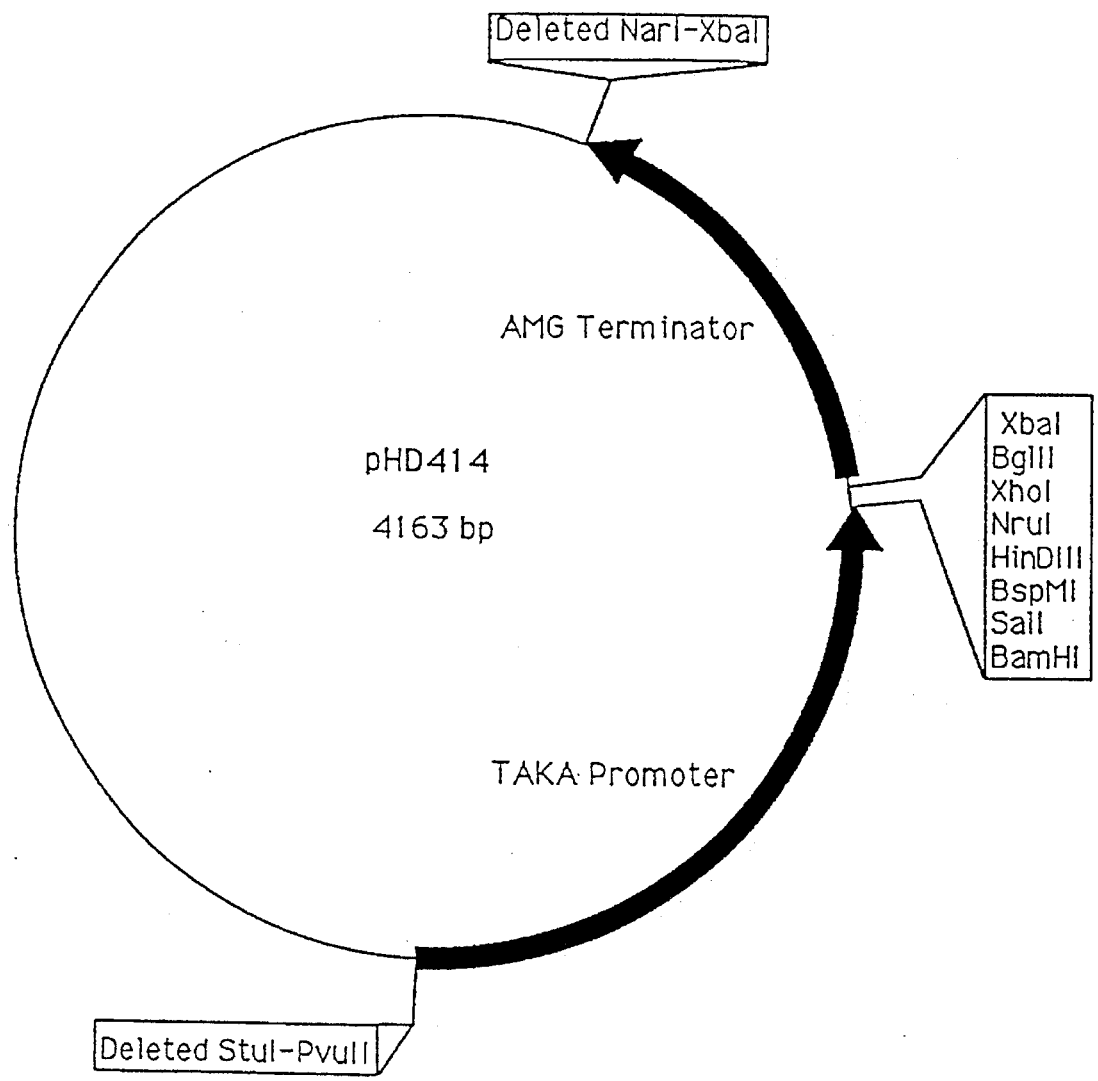
FIG. 10 shows the expression vector pHD414.

The vector pHD414 (FIG. 10) is a derivative of the plasmid p775 (described in EP 238 023). In contrast to this plasmid, pHD 414 has a string of unique restriction sites between the promoter and the terminator. The plasmid was constructed by removal of an approximately 200 bp long fragment (containing undesirable RE sites) at the 3'end of the terminator, and subsequent removal of an approximately 250 bp long fragment at the 5'end of the promoter, also containing undesirable sites. The 200 bp region was removed by cleavage with NarI (positioned in the pUC vector) and XbaI (just 3' to the terminator), subsequent filling in the generated ends with Klenow DNA polymerase +dNTP, purification of the vector fragment on gel and religation of the vector fragment. This plasmid was called pHD413. pHD413 was cut with StuI (positioned in the 5'end of the promoter) and PvuII (in the pUC vector), fractionated on gel and religated, resulting in pHD414. FIG. 10 is a map of plasmid pHD414, wherein "AMG Terminator" indicates the *A. niger* glucoamylase terminator, and "TAKA Promoter" indicates the *A. oryzae* TAKA amylase promoter. pHD464 is a derivative of pHD414, in which the 5' non-translated region is substituted by the 5' non-translated region from the Aspergillus TPi gene.

Construction of the RGAEse 1 expression cassette

Plasmid miniprep. DNA from pRGA1 was digested with BamHI and XhoI, electrophoresed in 0.7% agarose gel, followed by purification of the 1.0 kb cDNA insert using the Geneclean II kit according to the manufacturer's instructions (Bio 101 Inc., La Jolla) and ligation into BamHI/XhoI-cleaved pHD414 vector. One µl of the ligation mixture was electroporated into *E. coli* 1061 and two transformants analyzed by BamHI/XhoI digestion of plasmid miniprep. DNA. Since both clones (designated pRGA1 and pRGA2) contained a correct sized insert, pRGA1 was chosen for further experiments. A midi preparation of the pRGA1 expression plasmid (Qiagen Tip 100, see section 4) was checked by sequencing the 5'-end of the construct and used in *Aspergillus oryzae* transformation.

Transformation of *Aspergillus oryzae* and analysis of the transformants 100 ml of the Aspergillus minimal medium (1M sucrose, 10 mM urea, 0.52 mg/ml KCl, 0.52 mg/ml MgSO$_4$, 1.52 mg/ml KH$_2$PO$_4$, 0.04 µg/ml Na$_2$B$_4$O$_7$, 0.4 µg/ml CuSO$_4$, 0.8 µg/ml FePO$_4$, 0.8 µg/ml MnSO$_4$, 0.8 µg/ml Na$_2$MoO$_4$, 8 µg/ml ZnSO$_4$) was inoculated with spore suspensions from *A. oryzae* strains 1560 or 1560–710 or *A. niger*, the mycelium was collected by filtration through sterile Miracloth after 24 hours growth at 30° C., washed with 200 ml 0.6M MgSO$_4$, suspended in 25 ml of cold 1.2M MgSO$_4$, 10 mM NaH$_2$PO$_4$, pH 5.8 containing 2 mg/ml Novozym® (Novo Nordisk A/S) and incubated on ice for 5 minutes. One ml of BSA (12 mg/ml, sterile filtered) was added to the mycelia and the suspension was incubated at 37° C. for 1.5 hour with gentle shaking. Protoplasts were separated from undigested mycelia debris by filtering through Miracloth, overlayed with 5 ml 0.6M sorbitol, 100 mM Tris-HCl, pH 7.0, and centrifuged at 2500 rpm for 15 minutes. Protoplasts were collected from interphase, washed four times in 3 ml of 1.2M sorbitol, 10 mM Tris-HCl, pH 7.5, 10 mM CaCl$_2$, resuspended in the same buffer at a concentration of between $5 \times 10^7$–$5 \times 10^8$/ml and used immediately.

Transformation of *A. oryzae* or *A. niger* was carried out essentially as follows. Eight µg of Qiagen purified pRGA1 plasmid DNA (1 µg/µl) was mixed with 1 µg of Qiagen purified ToC 90 (1 µg/µl) co-plasmid DNA, an *A. nidulans* AmdS gene carrying plasmid, and 100 µl of protoplast suspension, and incubated at RT° for 20 minutes. 250 µl of 60% (w/v) PEG, 10 mM Tris-HCl, pH 7.5, 10 mM CaCl2 was added and the mixture incubated at RT° for 20 minutes. After addition of 3 ml 1.2M sorbitol, the transformation mixture was centrifuged at 2500 rpm for 10 minutes, resuspended in 100 µl 1.2M sorbitol, spread on AmdS selection plates and incubated at 30° C. for 3 to 5 days.

Twenty ml aliquots of YP+maltodextrin (2%) medium were inoculated with spore suspensions from AmdS$^+$ transformants cotransformed with the ToC plasmid (4 in *A. oryzae* 1560–710, 2 in the strain 1560), followed by growth at 30° C. for 2 to 3 days. The transformants were screened for RGAEse I activity by assaying the culture medium for rhamnogalacturonan acetylesterase and acetylesterase activities. The amount and purity of proteins secreted to the culture medium in various transformants was evaluated by analyzing 4 µl aliquots of the supernatant fractions on 10% SDS-PAGE (Fey et al. 1984) followed by either Coomassie or silver stain, using the purified RGAEse I enzyme preparation from *A. aculeatus* as a control.

Enzymatic assays

The acetylesterase activity in the culture medium of the AmdS$^+$ transformants was measured as increase of absorbance at OD$_{405}$ after incubation of 20 µl samples at 40° C. for 30 minutes in 500 µl of 2 mM p-nitrophenyl-acetate/20 mM Na-citrate buffer, pH 5.0 using culture medium from *A. oryzae* 1560–710 as a negative control and the purified RGAEse I preparation (0.78 mg/ml) as a positive control. Before measurement, the pH was raised by adding 1 ml of Tris-HCl, pH 7.0 to the samples. Due to a high acetylesterase activity in the control strain all samples exhibited a comparable activity towards p-nitrophenyl-acetate (data not shown) with no detectable increase in the AmdS$^+$ transformants.

Figure 11:
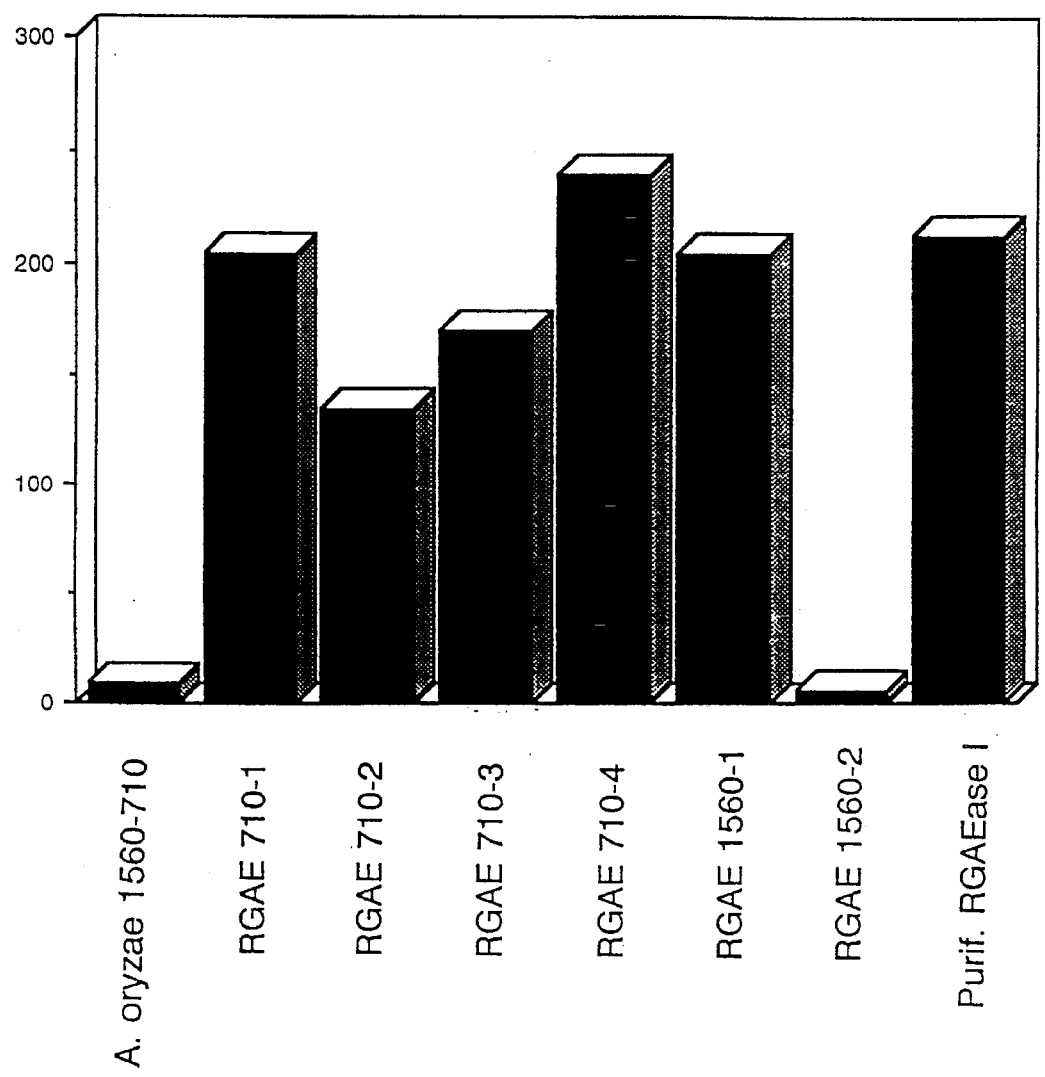
FIG. 11 shows the activity of a rhamnogalacturonan acetyl esterase from *A. aculeatus* towards 1% modified hairy regions (MHR).

The rhamnogalacturonan acetylesterase activity in the culture medium (see above) was measured as a release of acetate from modified hairy regions (MHR) isolated from apple pectin (Schols et al. 1990). The samples (50 µl of each supernatant) were incubated with 100 µl of 1% (w/v, in $H_2O$) modified hairy regions for a) 2 hours and b) 24 hours using the same control samples as above. The determination of acetic acid was carried out using the acetic acid kit from Boehringer Mannheim according to the manufacturer's instructions. Five out of six AmdS$^+$ transformants show a clear activity towards 1% MHR, while the sixth transformant exhibit no activity compared to the *A. oryzae* control strain 1560–710 (FIG. 11). FIG. 11 shows the activity towards 1% modified hairy regions (MHR), produced by recombinant *A. oryzae* strains expressing rhamnogalacturonan acetyl esterase I from *A. aculeatus*. The enzymatic activities were measured as a release of acetate from apple pectin MHR. The highest activities observed in the transformants RGAE 710-1 and RGAE 710-4 coincide with a ca. 35 kDa protein secreted into the culture medium. The protein is slightly overglycosylated compared to the purified RGAEse I from *A. aculeatus* as judged by SDS-PAGE.

Media

YPD: 10 g yeast extract, 20 g peptone, $H_2O$ to 810 mi. Autoclaved, 90 ml 20% glucose (sterile filtered) added.

YPG-agar: 25 g/l Bactoagar, 15 g/l glucose, 5 g/l $K_2PO_4$, 0.5 g/l $MgSO_4$–$7H_2O$, pH adjusted to 5.0. Autoclaved.

10×Basal salt: 66.8 g yeast nitrogen base, 100 g succinic acid, 60 g NaOH, $H_2O$ ad 1000 ml, sterile filtered.

SC-URA: 90 ml 10×Basal salt, 22.5 ml 20% casamino acids, 9 ml 1% tryptophane, $H_2O$ ad 806 ml, autoclaved, 3.6 ml 5% threonine and 90 ml 20% glucose added.

SC-H agar: 7.5 g/l yeast nitrogen base without amino acids, 11.3 g/l succinic acid, 6.8 g/l NaOH, 5.6 g/l casamino acids without vitamins, 0.1 g/l tryptophan and 20 g/l agar (Bacto). Autoclaved for 20 minutes at 121° C. After autoclaving, 55 ml of a 22% galactose solution and 1.8 ml of a 5% threonine solution were added per 450 ml agar.

YNB-1 agar: 3.3 g/l $KH_2PO_4$, 16.7 g/l agar, pH adjusted to 7. Autoclaved for 20 minutes at 121° C. After autoclaving, 25 ml of a 13.6% yeast nitrogen base without amino acids, 25 ml of a 40% glucose solution, 1.5 ml of a 1% L-leucine solution and 1.5 ml of a 1% histidine solution were added per 450 ml agar.

YNB-1 broth: Composition as YNB-1 agar, but without the agar.

MHR overlayer gel: 1% agarose, 0,5% MHR in 0,05M Na-acetate buffer, pH 4.5. The gel was boiled and then cooled to 55° C. before the overlayer was poured onto agar plates.

FG-4-Agar: 35 g/l agar, 30 g/l Soy bean meal, 15 g/l maltodextrin (Glucidex 6), 5 g/l Bacto pepton, pH 7. Autoclaved 40 minutes at 121° C.

FG-4 medium: 30 g/l Soy bean meal, 15 g/l maltodextrin (Glucidex 6), 5 g/l Bacto pepton. Autoclaved 40 minutes at 121° C.

MDU-2 medium: 45 g/l maltose, 1 g/l $MgSO_4$–7 $H_2O$, 1 g/l NaCl, 2 g/l $K_2SO_4$, 12 g/l $KH_2PO_4$, 0.1 ml/l Pluronic 61 L, 0.5 ml/l Trace metal solution. pH 5.0. Autoclaved 20 minutes at 121° C. 15 ml/l 50% sterile filteret urea is added after autoclavation.

Trace metal solution: 13.9 g/l $FeSO_4$–7 $H_2O$, 8.45 g/l $MnSO_4$–$H_2O$, 6.8 g/l $ZnCl_2$, 2.5 g/l $CuSO_4$–$5H_2O$, 0.24 g/l $NiCl_2$–$6H_2O$, 3 g/l citric acid.

For a better understanding of the invention reference is made to the following references.

Aviv, H. & Leder, P. 1972. Proc. Natl. Acad. Sci. U.S.A. 69: 1408–1412.

Becker, D. M. & Guarante, L. 1991. Methods Enzymol. 194: 182–187.

Chirgwin, J. M., Przybyla, A. E., MacDonald, R. J. & Rutter, W. J. 1979. Biochemistry 18: 5294–5299.

Feinberg, A. P. & Vogelstein, B. 1983. Anal. Biochem. 132: 6–13.

Fey, S., Mose Larsen, P. & Biskjaer, N. L. 1984. Ph.D. thesis, Faculty of Natural Sciences, Aarhus University, Denmark.

Gubler, U. & Hoffman, B. J. 1983. Gene 25: 263–269.

Hanahan, D. 1985. in DNA Cloning, (Glover, D. M., ed.) IRL, Oxford, Vol. 1., pp. 109–135.

Ohara, O., Dorit, R. L. & Gilbert, W. 1989. Proc. Natl. Acad. Sci. U.S.A. 86:5673–5677.

Sambrook, J., Fritsch, E. F. & Maniatis, T. 1989. Molecular Cloning: A Laboratory Manual. Cold Spring Harbor Lab., Cold Spring Harbor, N.Y.

Sanger, F., Nicklen, S. & Coulson, A. R. 1977. Proc. Natl. Acad. Sci. U.S.A. 74: 5463–5467.

Schols, H. A., Geraeds, C. C. J. M., Searle-van Leeuwen, M. J. F., Kormelink, F. J. M. & Voragen, A. G. J. 1990. Carbohydrate Res. 206: 105–115.

Southern, E. M. 1975. J. Mol. Biol. 98: 503–517.

---

We claim:

1. A substantially purified rhamnogalacturonan acetyl esterase which is endogenous to an *Aspergillus aculeatus* strain.

2. A substantially purified rhamnogalacturonan acetyl esterase according to claim 1 which has (a) a pH optimum in the range of 4.0–7.0; and (b) a temperature optimum between 10° and 50° C.

3. A rhamnogalacturonan acetyl esterase according to claim 2 which has (a) a pH optimum in the range of 4.5–6.0; and (b) a temperature optimum between 25° and 45° C.

4. A substantially purified rhamnogalacturonan acetyl esterase according to claim 1 which has an isoelectric point in the range of 3.7–4.7 and a molecular weight in the range of between 30,000 and 50,000.

5. A substantially purified rhamnogalacturonan acetyl esterase according to claim 4 which has an isoelectric point in the range of 4.0–4.5.

6. A rhamnogalacturonan acetyl esterase according to claim 1 which is encoded by a DNA segment which hybridizes to the coding region of SEQ ID NO:10 by presoaking in 5×SSC and prehybridizing for 1 hour at ~40° C. in a solution of 5×SSC, 5×Denhardt's solution, 50 mM sodium phosphate, pH 6.8, and 50 µg of denatured sonicated calf thymus DNA, and hybridizing in the same solution supplemented with 50 µCi 32-P-dCTP labelled probe for 18 hours at ~40° C.

7. A rhamnogalacturonan acetyl esterase according to claim 1, wherein the strain is CBS 101.43.

8. A rhamnogalacturonan acetyl esterase according to claim 1 which is encoded by a DNA segment comprising the DNA sequence SEQ ID NO: 10.

9. A rhamnogalacturonan acetyl esterase according to claim 1 having the following partial amino acid sequence

```
1                5                10               15
Asp—Arg—Val—Tyr—Leu—Ala—Gly—Asp—Ser—Thr—Met—Thr—Lys—Asn—Gly—

20               25
Gly—Xaa—Ser—Gly—Thr—Asn—Gly—Trp—Gly—Glu—Tyr—Leu—Ala—   (SEQ ID NO: 1).
```

10. An isolated DNA segment comprising a DNA sequence encoding a rhamnogalacturonan acetyl esterase according to claim 1.

11. A DNA segment according to claim 10, wherein the DNA sequence hybridizes to the coding region of SEQ ID NO:10 by presoaking in 5×SSC and prehybridizing for 1 hour at ~40° C. in a solution of 5×SSC, 5×Denhardt's solution, 50 mM sodium phosphate, pH 6.8, and 50 µg of denatured sonicated calf thymus DNA, and hybridizing in the same solution supplemented with 50 µCi 32-P-dCTP labelled probe for 18 hours at ~40° C.

12. A DNA segment according to claim 10, wherein the DNA sequence is:

| | | | | | |
|---|---|---|---|---|---|
| AGTCTATAAG | AAGATTGACA | GCCAAGAACA | CCACCCACAA | TGAAGACCGC | CGCCTCTTGC |
| ACCGCTCTTC | TTCCTCCCCT | CTGCCCTCGC | CACGACNNGG | TCTATCTCGC | GGGTGACTCG |
| ACCATGGCCA | AGAATGGAGG | CGGGTCGGGA | ACTAACGGCT | GGGGCGAGTA | CCTCGCCAGT |
| TACCTCTCCG | CGACAGTGGT | TAACGACGCG | GTCGCGGCC | GCAGCGCGCG | CTCGTACACA |
| CGCGAGGGTC | GGTTCGAGAA | CATCGCCGAT | GTAGTGACGG | CGGGCGACTA | CGTGATCGTC |
| GAGTTCGGCC | ACAACGACGG | TGGCTCGCTG | TCCACGGACA | ATGGACGCAC | CGACTGCTCC |
| GGTACCGGGG | CAGAAGTCTG | CTATAGCGTC | TACGACGGGG | TCAACGAGAC | CATCCTCACC |
| TTCCCCGCCT | ACCTGGAGAA | CGCCGCCAAG | CTGTTCACCG | CCAAGGGCGC | CAAGGTCATT |
| CTCAGCAGCC | AGACCCCCAA | CAACCCCTGG | GAGACCGGCA | CCTTCGTCAA | CTCCCCCACG |
| CGCTTCGTTG | AGTACGCCGA | GCTGGCCGCC | GAGGTCGCTG | GCGTCGAGTA | CGTCGACCAC |
| TGGTCCTACG | TGGACAGCAT | CTATGAGACC | TTGGCAATGC | CACCGTCAAC | TCGTATTCCC |
| CATCGATCAC | ACCCACACCA | GTCCTGCGGC | GCGAGGTCGT | GGCTGAGCGT | TCTTGAAGGC |
| GGTGGTATGC | ACGGGTACGT | CGTTGAAGAG | TGTGTTGACG | ACGACGAGCT | TTGAGGGGAC |
| ATGTCTGTGA | TTGAGCAGAT | GGAAAGACAA | AGGAGTGGAC | GGATAAGGAC | AGGAGTTGTC |
| ATGTATAGTG | GTAGTTTGTG | CATTGCAAAT | GGTATCTGAA | CTGGCTCGCT | TATGCTCATG |
| ATCGACAAAA | AAAAAAAAAA | AAAAAAAAAA | AAAAA | (SEQ ID NO: 10). | |

13. A vector comprising a DNA sequence according to claim 10.

14. A vector according to claim 13, further comprising an *Aspergillus oryzae* taka-amylase promoter.

15. A transformed host cell comprising a vector according to claim 13.

16. A transformed host cell according to claim 15, wherein the transformed host cell is an Aspergillus strain.

17. A transformed host cell according to claim 15, wherein the transformed host cell is a strain of *Aspergillus aculeatus, Aspergillus niger, Aspergillus oryzae* or *Aspergillus awamori*.

18. A transformed host cell according to claim 15, wherein the transformed host cell is a strain of Bacillus sp., *E. coli* or *S. cerevisiae*.

19. A method for producing a rhamnogalacturonan acetyl esterase, comprising (a) culturing a transformed host cell according to claim 15 under conditions conducive to expression of the rhamnogalacturonan acetyl esterase; and (b) recovering the rhamnogalacturonan acetyl esterase.

20. An enzyme preparation, comprising a rhamnogalacturonan acetyl esterase according to claim 1 and a pectinase preparation which is useful for degrading or modifying plant cell walls.

21. An enzyme preparation according to claim 20, wherein the pectinase preparation is derived from Aspergillus.

22. An enzyme preparation according to claim 21, wherein the pectinase preparation is derived from *Aspergillus niger, Aspergillus aculeatus, Aspergillus awamori* or *Aspergillus oryzae*.

23. A method of degrading or modifying acetylated, branched rhamnogalacturonan, comprising treating the acetylated, branched rhamnogalacturonan with a rhamnogalacturonan acetyl esterase according to claim 1.

24. A method according to claim 23, wherein the acetylated, branched rhanmogalacturonan is present on plant cell walls.

25. A method according to claim 23, wherein the rhamnogalacturonan acetyl esterase is used together with a rhamnogalacturonase and/or an acetyl esterase.

26. A method of degrading or modifying an acetylated, branched rhamnogalacturonan, comprising treating the acetylated, branched rhamnogalacturonan with an enzyme preparation according to claim 20.

27. A method according to claim 26, wherein the acetylated, branched rhanmogalacturonan is present on plant cell walls.

28. A method according to claim 26, wherein the enzyme preparation is used together with a rhamnogalacturonase and/or an acetyl esterase.

* * * * *

SEQUENCE LISTING ( 1 ) GENERAL INFORMATION:

( i i i ) NUMBER OF SEQUENCES: 18

( 2 ) INFORMATION FOR SEQ ID NO: 1:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide (vi) ORIGINAL SOURCE:
    (A) ORGANISM: Aspergillus aculeatus
    (B) STRAIN: CBS 101.43

(xi) SEQUENCE DESCRIPTION: SEQ ID NO: 1:

Asp Arg Val Tyr Leu Ala Gly Asp Ser Thr Met Thr Lys Asn Gly Gly
1               5                   10                  15

Xaa Ser Gly Thr Asn Gly Trp Gly Glu Tyr Leu Ala
            20              25

(2) INFORMATION FOR SEQ ID NO: 2:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

ATGAAGACCG CCGCCTCTTG CACCGCTCTT CTTCCTCCCC TCTGCCCTCG CCACGACNNG          60

(2) INFORMATION FOR SEQ ID NO: 3:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cNA (xi) SEQUENCE DESCRIPTION: SEQ ID NO: 3:

GTCTATCTCG CGGGTGACTC GACCATGGCC AAGAATGGAG GCGGGTCGGG AACTAACGGC          60

(2) INFORMATION FOR SEQ ID NO: 4:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

TGGGGCGAGT ACCTGCGAGT TACCTCTCCG CGACAGTGGT TAACGACGCG GTCGCG            56

(2) INFORMATION FOR SEQ ID NO: 5:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

GACGCAACCT ATGAAGACCT TGGAATGCCA CCGTCAACTC GTATTCCCCA TCGATCACAC          60

(2) INFORMATION FOR SEQ ID NO: 6:

(i) SEQUENCE CHARACTERISTICS:
        (A) LENGTH: 60 base pairs
        (B) TYPE: nucleic acid
        (C) STRANDEDNESS: single
        (D) TOPOLOGY: linear ( i i ) MOLECULE TYPE: cDNA ( x i ) SEQUENCE DESCRIPTION: SEQ ID NO: 6:

| CCACACCAGT | CCTGCGGCGC | GAGGTCGTGG | CTGAGCGTTC | TTGAAGGCGG | TGGTATGCAC | 60 |

(2) INFORMATION FOR SEQ ID NO: 7:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 7:

| GGGTACGTCG | TTGAAGAGTG | TGTTGACGAC | GACGAGCTT | | | 39 |

(2) INFORMATION FOR SEQ ID NO: 8:

( i ) SEQUENCE CHARACTERISTICS:
        ( A ) LENGTH: 176 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 8:

| ATGAAGACCG | CCGCCTCTTG | CACCGCTCTT | CTTCCTCCCC | TCTGCCCTCG | CCACGACNNG | 60 |
| GTCTATCTCG | CGGGTGACTC | GACCATGGCC | AAGAATGGAG | GCGGGTCGGG | AACTAACGGC | 120 |
| TGGGGCGAGT | ACCTGCGAGT | TACCTCTCCG | CGACAGTGGT | TAACGACGCG | GTCGCG | 176 |

(2) INFORMATION FOR SEQ ID NO: 9:

( i ) SEQUENCE CHARACTERISTICS:
        ( A ) LENGTH: 159 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 9:

| GACGCAACCT | ATGAAGACCT | TGGAATGCCA | CCGTCAACTC | GTATTCCCCA | TCGATCACAC | 60 |
| CCACACCAGT | CCTGCGGCGC | GAGGTCGTGG | CTGAGCGTTC | TTGAAGGCGG | TGGTATGCAC | 120 |
| GGGTACGTCG | TTGAAGAGTG | TGTTGACGAC | GACGAGCTT | | | 159 |

(2) INFORMATION FOR SEQ ID NO: 10:

( i ) SEQUENCE CHARACTERISTICS:
        ( A ) LENGTH: 935 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 10:

| AGTCTATAAG | AAGATTGACA | GCCAAGAACA | CCACCCACAA | TGAAGACCGC | CGCCTCTTGC | 60 |
| ACCGCTCTTC | TTCCTCCCCT | CTGCCCTCGC | CACGACNNGG | TCTATCTCGC | GGGTGACTCG | 120 |
| ACCATGGCCA | AGAATGGAGG | CGGGTCGGGA | ACTAACGGCT | GGGGCGAGTA | CCTCGCCAGT | 180 |
| TACCTCTCCG | CGACAGTGGT | TAACGACGCG | GTCGCGGGCC | GCAGCGCGCG | CTCGTACACA | 240 |

```
CGCGAGGGTC  GGTTCGAGAA  CATCGCCGAT  GTAGTGACGG  CGGGCGACTA  CGTGATCGTC    300

GAGTTCGGCC  ACAACGACGG  TGGCTCGCTG  TCCACGGACA  ATGGACGCAC  CGACTGCTCC    360

GGTACCGGGG  CAGAAGTCTG  CTATAGCGTC  TACGACGGGG  TCAACGAGAC  CATCCTCACC    420

TTCCCCGCCT  ACCTGGAGAA  CGCCGCCAAG  CTGTTCACCG  CCAAGGGCGC  CAAGGTCATT    480

CTCAGCAGCC  AGACCCCCAA  CAACCCCTGG  GAGACCGGCA  CCTTCGTCAA  CTCCCCCACG    540

CGCTTCGTTG  AGTACGCCGA  GCTGGCCGCC  GAGGTCGCTG  GCGTCGAGTA  CGTCGACCAC    600

TGGTCCTACG  TGGACAGCAT  CTATGAGACC  TTGGCAATGC  CACCGTCAAC  TCGTATTCCC    660

CATCGATCAC  ACCCACACCA  GTCCTGCGGC  GCGAGGTCGT  GGCTGAGCGT  TCTTGAAGGC    720

GGTGGTATGC  ACGGGTACGT  CGTTGAAGAG  TGTGTTGACG  ACGACGAGCT  TTGAGGGGAC    780

ATGTCTGTGA  TTGAGCAGAT  GGAAAGACAA  AGGAGTGGAC  GGATAAGGAC  AGGAGTTGTC    840

ATGTATAGTG  GTAGTTTGTG  CATTGCAAAT  GGTATCTGAA  CTGGCTCGCT  TATGCTCATG    900

ATCGACAAAA  AAAAAAAAA   AAAAAAAAA   AAAAA                                 935
```

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
CTGTAATACG  ACTCACTA                                                       18
```

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
ATTACATGAT  GCGGCCCT                                                       18
```

( 2 ) INFORMATION FOR SEQ ID NO:13:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 14
        ( D ) OTHER INFORMATION: /mod_base= i ( i x ) FEATURE:
        ( A ) NAME/KEY: modified_base
        ( B ) LOCATION: 17
        ( D ) OTHER INFORMATION: /mod_base= i ( i x ) FEATURE:
        ( A ) NAME/KEY: modified_base
        ( B ) LOCATION: 23
        ( D ) OTHER INFORMATION: /mod_base= i ( i x ) FEATURE:
        ( A ) NAME/KEY: modified_base
        ( B ) LOCATION: 32
        ( D ) OTHER INFORMATION: /mod_base= i (xi) SEQUENCE DESCRIPTION: SEQ ID NO:13:

```
GGAATTCC GAY WSN ACN ATG GCN AAR AAY GGN GG                          34
         Asp Ser Thr Met Ala Lys Asn Gly Gly
                             5
```

(2) INFORMATION FOR SEQ ID NO:14:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:14:

```
Asp Ser Thr Met Ala Lys Asn Gly Gly
                 5
```

(2) INFORMATION FOR SEQ ID NO:15:

(i) SEQUENCE CHARACTERISTICS:
        (A) LENGTH: 216 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 40..216

(ix) FEATURE:
        (A) NAME/KEY: sig_peptide
        (B) LOCATION: 40..93

(ix) FEATURE:
        (A) NAME/KEY: mat_peptide
        (B) LOCATION: 94..216

(xi) SEQUENCE DESCRIPTION: SEQ ID NO:15:

```
AGTCTATAAG AAGATTGACA GCCAAGAACA CCACCCACA ATG AAG ACC GCC GCC       54
                                           Met Lys Thr Ala Ala
                                           -18         -15

TCT TGC ACC GCT CTT CTT CCT CCC CTC TGC CCT CGC CAC GAC NNG GTC     102
Ser Cys Thr Ala Leu Leu Pro Pro Leu Cys Pro Arg His Asp Xaa Val
            -10             -5                           1

TAT CTC GCG GGT GAC TCG ACC ATG GCC AAG AAT GGA GGC GGG TCG GGA     150
Tyr Leu Ala Gly Asp Ser Thr Met Ala Lys Asn Gly Gly Gly Ser Gly
        5                10                  15

ACT AAC GGC TGG GGC GAG TAC CTG CGA GTT ACC TCT CCG CGA CAG TGG     198
Thr Asn Gly Trp Gly Glu Tyr Leu Arg Val Thr Ser Pro Arg Gln Trp
 20              25                  30                      35

TTA ACG ACG CGG TCG CGG                                             216
Leu Thr Thr Arg Ser Arg
             40
```

(2) INFORMATION FOR SEQ ID NO:16:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO:16:

```
Met Lys Thr Ala Ala Ser Cys Thr Ala Leu Leu Pro Pro Leu Cys Pro
-18         -15             -10                     -5

Arg His Asp Xaa Val Tyr Leu Ala Gly Asp Ser Thr Met Ala Lys Asn
```

```
                     1                         5                                  1 0
Gly  Gly  Gly  Ser  Gly  Thr  Asn  Gly  Trp  Gly  Glu  Tyr  Leu  Arg  Val  Thr
 15                       20                       25                        30

Ser  Pro  Arg  Gln  Trp  Leu  Thr  Thr  Arg  Ser  Arg
                     35                       40
```

( 2 ) INFORMATION FOR SEQ ID NO:17:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..162

( x i ) SEQUENCE DESCRIPTION: SEQ ID NO:17:

```
GAC  GCA  ACC  TAT  GAA  GAC  CTT  GGA  ATG  CCA  CCG  TCA  ACT  CGT  ATT  CCC       48
Asp  Ala  Thr  Tyr  Glu  Asp  Leu  Gly  Met  Pro  Pro  Ser  Thr  Arg  Ile  Pro
 1                        5                        10                       15

CAT  CGA  TCA  CAC  CCA  CAC  CAG  TCC  TGC  GGC  GCG  AGG  TCG  TGG  CTG  AGC       96
His  Arg  Ser  His  Pro  His  Gln  Ser  Cys  Gly  Ala  Arg  Ser  Trp  Leu  Ser
                     20                       25                       30

GTT  CTT  GAA  GGC  GGT  GGT  ATG  CAC  GGG  TAC  GTC  GTT  GAA  GAG  TGT  GTT      144
Val  Leu  Glu  Gly  Gly  Gly  Met  His  Gly  Tyr  Val  Val  Glu  Glu  Cys  Val
               35                       40                       45

GAC  GAC  GAC  GAG  CTT  TGA  GGGGACATGT  CTGTGATTGA  GCAGATGGAA                     192
Asp  Asp  Asp  Glu  Leu
               50

AGACAAAGGA  GTGGACGGAT  AAGGACAGGA  GTTGTCATGT  ATAGTGGTAA  TCGACAAAAA              252

AAAAAAAAAA  AAAAAAAAAA  AAAA                                                         276
```

( 2 ) INFORMATION FOR SEQ ID NO:18:

( i ) SEQUENCE CHARACTERISTICS:
        ( A ) LENGTH: 53 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Asp  Ala  Thr  Tyr  Glu  Asp  Leu  Gly  Met  Pro  Pro  Ser  Thr  Arg  Ile  Pro
 1                        5                        10                       15

His  Arg  Ser  His  Pro  His  Gln  Ser  Cys  Gly  Ala  Arg  Ser  Trp  Leu  Ser
                     20                       25                       30

Val  Leu  Glu  Gly  Gly  Gly  Met  His  Gly  Tyr  Val  Val  Glu  Glu  Cys  Val
               35                       40                       45

Asp  Asp  Asp  Glu  Leu
               50
```